(12) United States Patent
Blankenstein

(10) Patent No.: US 7,138,269 B2
(45) Date of Patent: Nov. 21, 2006

(54) MICROFLOW SYSTEM FOR PARTICLE SEPARATION AND ANALYSIS

(75) Inventor: Gert Blankenstein, Hamburg (DE)

(73) Assignee: Inverness Medical Switzerland GmbH, Zug (CH)

( * ) Notice: Subject to any disclaimer, the term of this patent is extended or adjusted under 35 U.S.C. 154(b) by 757 days.

(21) Appl. No.: 10/192,996

(22) Filed: Jul. 9, 2002

(65) Prior Publication Data

US 2003/0044832 A1    Mar. 6, 2003

Related U.S. Application Data

(62) Division of application No. 09/254,310, filed as application No. PCT/DK97/00368 on Sep. 4, 1997, now Pat. No. 6,432,630.

(30) Foreign Application Priority Data

Sep. 4, 1996   (DK) .................... 0953/96
Feb. 10, 1997  (DK) .................... 0150/97

(51) Int. Cl.
    *C12M 1/34*    (2006.01)
(52) U.S. Cl. ............ 435/287.2; 422/50; 422/51; 422/68.1; 422/82.05; 422/82.08; 422/186; 422/186.1; 435/287.1; 435/287.3; 436/514; 436/518; 436/526
(58) Field of Classification Search ............ 422/50, 422/51, 68.1, 82.05, 82.08, 186, 186.1; 435/287.1, 435/287.2, 287.3; 436/514, 518, 526
    See application file for complete search history.

(56) References Cited

U.S. PATENT DOCUMENTS

| | | | |
|---|---|---|---|
| 3,560,754 A | 2/1971 | Kamentsky et al. | |
| 3,827,555 A | 8/1974 | Kamentsky et al. | |
| 4,279,345 A | 7/1981 | Allred | |
| 4,738,773 A | 4/1988 | Muller-Ruchholtz et al. | |
| 4,756,427 A | 7/1988 | Gohde et al. | |
| 4,894,146 A | 1/1990 | Giddings | |
| 4,910,148 A | 3/1990 | Sorensen et al. | |
| 5,039,426 A | 8/1991 | Giddings | |
| 5,053,344 A | 10/1991 | Zborowski et al. | |
| 5,123,901 A | 6/1992 | Carew | |
| 5,304,487 A | 4/1994 | Wilding et al. | |
| 5,460,797 A | 10/1995 | Ryan | |
| 5,465,849 A | 11/1995 | Wada et al. | |
| 5,483,469 A | 1/1996 | Van den Engh et al. | |
| 5,674,743 A | 10/1997 | Ulmer | |
| 5,811,099 A | 9/1998 | Ryan | |

FOREIGN PATENT DOCUMENTS

| | | |
|---|---|---|
| DE | 38 27 252 | 2/1990 |
| EP | 0 196 205 | 10/1986 |
| EP | 0 454 286 | 10/1991 |
| EP | 0 736 765 | 10/1996 |
| WO | WO 91/15750 | 10/1991 |
| WO | WO 93/22058 | 11/1993 |
| WO | WO 94/15193 | 7/1994 |
| WO | WO 96/09409 | 3/1996 |

OTHER PUBLICATIONS

Blankenstein, Gert, "Microfabricated Flow System for Magnetic Cell and Particle Separation," *Scientific and Clinical Applications of Magnetic Carriers* edited by Häfeli, et al., Plenum Press, New York, 1997.

Nakamura, Noriyuki, et al., "Detection and Removal of *Escherichia coli* Using Fluorescein Isothiocyanate Conjugated Monoclonal Antibody Immobilized on Bacterial Magnetic Particles," *Anal Chem.* 1993, 65, 2036-2039.

Tondra, Mark, et al., "Design of Integrated Microfluidic Device for Sorting Magnetic Beads in Biological Assays."

Zborowski, Maciej, et al., "Continuous-Flow Magnetic Cell Sorting Using Soluble Imunomagnetic Label," *Scientific and Clinical Applications of Magnetic Carriers* edited by Häfeli, et al., Plenum Press, New York, 1997.

Ahn, C.H. et al., "A Fully Integrated Micromachined Magnetic Particle Manipulator and Separator", Proceeding of the workshop on Micro Electro Mechanical systems (MEM. OISO) Jan. 25-28, 1994, No. Workshop 7, Jan. 25, 1994, Institute of Electrical and Electronics Engineers, pp. 91-96.

Melamed et al., Flow Cytometry and Sorting, (Ed. Melamed et. Al., Wiley & Sons Inc., 1990, pp. 1-9 and 11-25.

Lea et al. (1990). Microspheres as immunoreagents for call identification and cell fractination. In Flow Cytometry and Sorting (eds. Melamed et al.) New York: Wiley-Liss. pp. 367-380.

Lett et al. (1990). Ultrasensitive molecular-level flow cytometry. In Flow Cytometry and Sorting (eds. Melamed et al.). New york: Wiley-Liss. pp. 381-396.

Kachel et al. (1990). Hydrodynamic properties of flow cytometry instruments. In Flow Cytometry and Sorting (eds. Melamed et al.). New York: Wiley-Liss. pp. 27-44.

Blankenstein et al. (1998). Modular concept of a laboratory on a chip for chemical and biochemical analysis. Biosen. Bioelectro. 13(3-4): 427-438.

Sun et al. (1998). Continuous, flow-through immunomagnetic cell sorting in a quadrupole filed. Cytometry. 33:469-475.

Hodder et al. (1997), Microfabricated flow chamber for fluorescence-based chemistries and stopped flow injection cytometry. Analyst. 122-883-887.

Moore et al. (1998). Lymphocyte fractionation using immunomagnetic colloid and a dipole magnet flow cell sorter. J. Biochem. Biophys. Methods. 37:11-33.

Hartig et al. (1992). Preparative continuous separation of biological particles by means of free-flow magnetophoresis in a free-flow electrophresis chamber. Electrophoresis. 13:674-676.

Zborowski et al. (1996). Magnetic flow sorting using a model system of human lymphocytes and a colloidal magnetic label. ASAIO J. 42(5):M666-671.

*Primary Examiner*—Christopher L. Chin
(74) *Attorney, Agent, or Firm*—Scott E. Kamholz; Foley Hoag LLP

(57) ABSTRACT

A micro flow system is provided for separating particles, comprising a microfabricated member having a flow channel (5) defined therein for guiding a flow of a fluid containing the particles through the flow channel, first inlet means (2) positioned at one end of the flow channel for entering the fluid into the flow channel, first outlet means (7) positioned at the other end of the flow channel for discharging the fluid from the flow channel, the flow of the fluid containing the particles being controlled in such a way that one particle at the time passes a cross section of the flow channel, the member being positioned in a field that is substantially perpendicular to a longitudinal axis of the flow channel so that particles residing in the flow channel and being susceptible to the field across the flow channel are deflected in the direction of the field. Further, a micro flow system is provided for analyzing components of a fluid comprising a microfabricated member having a flow channel defined therein for guiding a flow of a fluid through the flow channel, first inlet means for entering particles into the flow channel, first outlet means for discharging of fluid from the flow channel and a plurality of assay sites located in the flow channel and comprising immobilized reagents whereby the fluid may be analyzed for a plurality of components while residing in the flow channel.

10 Claims, 14 Drawing Sheets

MICROFLOW SYSTEM FOR PARTICLE SEPARATION AND ANALYSIS

FIELD OF THE INVENTION

The present invention relates to methods and apparatuses for detection, separation, sorting, and analysis of particles, such as cells, cell organelles, beads, molecules, such as Deoxyribonucleic acid (DNA), proteins, etc. in a fluid. In particular, the invention relates to particle separation by using different forces such as magnetic, electrophoretic, hydrodynamic and/or gravitational forces, e.g for utilisation in flow cytometry, light microscopy, electrophoretic separation, magnetophoresis, etc.

BACKGROUND OF THE INVENTION

Flow cytometry is a well known technique that is used for high throughput measurements of optical and/or electrical characteristics of microscopic biological samples. Flow cytometry instruments analyse and isolate cells and organelles with particular physical, biochemical, and immunological properties.

Traditionally, cell sorting by flow cytometry (fluorescence activated cell sorting) has been the method of choice for isolation of specific cell populations by surface markers. However, cell sorting by flow cytometry suffers from several drawbacks, especially high dilution of desired cell sample, low speed and sterility problems. Furthermore, the equipment is very costly with high operation and maintenance cost, making the technique available only to a limited number of laboratories.

During the last few years, isolation of cells by antibody-coupled magnetic beads and carriers has been developed into a reliable tool for the isolation and characterisation of cell populations. Immunomagnetic cell separation, e.g. as commercially introduced by Dynal A/S and Miltenyi Biotec, has become an established method for cell analysis in clinical diagnostics. Due to the relatively low prize, this method is attractive in flow cytometry, especially in sorting of rare cellular events. For example, sorting of fetal cells contained in maternal blood sample provides a non-invasive alternative to prenatal diagnostic procedures, such as amniocentesis of chorionic villus sampling. Another rare event scenario is the detection of low concentration of cancer cells which has an important role in diagnosis of minimal residual disease and evaluation of appropriate therapies. Another medical application for cell sorting systems is the diagnosis of bacterial and viral diseases.

Although this method offers relatively inexpensive approach to sort rare cellular event, it adds considerable time onto the overall rare event detection and it does not offer the multiparameter analysis readily available with flow cytometry techniques. Existing techniques for magnetic separation are suffering from the low purity of the sorted cell fraction and the low recovery rate of the sorted cells. In most systems several washing steps have to be implemented into the separation procedure which then causes cell losses. Additionally small subpopulation of labelled cells cannot be directly isolated by existing magnetic separation techniques.

A good overview about fluorescence activated cell sorting procedures and magnetic activated cell sorting is given in Melamed et. al., "Flow Cytometry and Sorting, (Ed. Melamed et. al., Wiley & Sons Inc., 1990).

SUMMARY OF THE INVENTION

Advances in microfabrication and microfluidic technologies continue to fuel further investigation into the miniaturisation of bioanalytical instruments and biochemical assays in general. The present invention relates to development of a low cost non-invasive diagnostic test method and devices for carrying out such tests that include measuring, monitoring, sorting and analysing samples containing particles, such as organic cells, microbeads, cell organells and macromolecules such as DNA. The present invention provides a cheap, fast and reliable method and devices for handling, sorting and analysis of such particles.

Separation may be performed according to various physical properties, such as fluorescent properties or other optical properties, magnetic properties, density, electrical properties, etc. According to an important aspect of the invention, particle separation is performed by aligning the particles in one row of particles in a micro flow channel so that particles can be treated individually.

Thus, it is an object of the present invention to provide a micro flow system and a method of particle separation having an improved efficiency of particle separation compared to the prior art.

It is another object of the present invention to provide a micro flow system and a method for particle separation in which cell lysis is minimised.

It is yet another object of the present invention to provide an improved method for preparation of fluids containing particles for separation and analysis of the particles.

It is a still further object of the present invention to provide a micro flow system and a method for simultaneous separation of particles into a plurality of groups of particles.

It is a still further object of the present invention to provide a micro flow system including facilities for pre-treatment and/or post-treatment of a sample.

It is a still further objective of the invention is develop a system for separation and analysis of fetal cells in whole maternal blood samples using an integrated automated micro flow system. The system is designed by downscaling and combining different methods for handling, manipulation and analysis of biochemical samples. Thus, prenatal diagnostics by analysis of fetal cells separated from a whole maternal blood sample is an area, which can benefit from advances in miniaturisation.

It is another objective of the invention is develop a system for separation and analysis of cancer cells from a sample containing cancer cells and healthy cells using an integrated automated micro flow system. The system is also designed by downscaling and combining different methods for handling, manipulation and analysis of biochemical samples. Thus, cancer diagnostics by analysis of cancer cells separated from healthy cells is also an area which can benefit from advances in miniaturisation.

According to a first aspect of the invention the above and other objects are fulfilled by a micro flow system for separating particles, comprising a member having a flow channel defined therein for guiding a flow of a fluid containing the particles through the flow channel, first inlet means positioned at one end of the flow channel for entering the fluid into the flow channel, first outlet means positioned at the other end of the flow channel for discharging the fluid from the flow channel, the flow of the fluid containing the particles being controlled in such a way that one particle at the time passes a cross-section of the flow channel, the member being positioned in a field that is substantially perpendicular to a longitudinal axis of the flow channel so that particles residing in the flow channel and being susceptible to the field across the flow channel are deflected in the direction of the field.

According to a second aspect of the invention the above and other objects are fulfilled by a method of separating particles, comprising the steps of guiding a flow of a fluid containing the particles through a flow channel in such a way that one particle at the time passes a cross-section of the flow channel, positioning the flow channel in a field that is substantially perpendicular to a longitudinal axis of the flow channel so that particles residing in the flow channel and being susceptible to the field across the flow channel are deflected in the direction of the field and thereby separated from the fluid.

According to a third aspect of the invention the above and other objects are fulfilled by a micro flow system for separating particles, comprising a member having a flow channel defined therein for guiding a flow of a fluid containing the particles through the flow channel, first inlet means positioned at one end of the flow channel for entering the fluid into the flow channel, first and second outlet means positioned at the other end of the flow channel for discharging of fluid from the flow channel, the flow of the fluid containing the particles being controlled in such a way that one particle at the time passes a cross-section of the flow channel, monitoring means positioned at the flow channel for monitoring parameters of a particle residing within a measurement volume within the flow channel and providing an output signal corresponding to a monitored parameter, control means for controlling passage of fluid through the first and the second outlet means, respectively, in response to the output signal of the monitoring means whereby particles may be separated according to values of a parameter monitored by the monitoring means.

According to a fourth aspect of the invention the above and other objects are fulfilled by a method of separating particles, comprising the steps of guiding a flow of a fluid containing the particles through a flow channel in such a way that one particle at the time passes a cross-section of the flow channel, the flow channel having first and second outlet means for discharging of fluid from the flow channel, monitoring parameters of a particle residing within a measurement volume within the flow channel and controlling passage of fluid through the first and the second outlet means, respectively, in response to a monitored parameter value whereby particles may be separated according to values of a monitored parameter.

According to a preferred embodiment of the invention, a method of separating fetal cells from maternal cells, comprising the steps of selective magnetically staining of fetal cells in a fluid containing fetal and maternal cells, guiding a flow of the fluid containing the fetal cells through a flow channel in such a way that one fetal cell at the time passes a cross-section of the flow channel, positioning the flow channel in a magnetic field that is substantially perpendicular to a longitudinal axis of the flow channel so that magnetically stained fetal cells residing in the flow channel are deflected in the direction of the magnetic field.

Further a method is provided for separating cancer cells from other cells, comprising the steps of selective magnetically staining of cancer cells in a fluid containing cancer and other cells, guiding a flow of the fluid containing the cancer cells through a flow channel in such a way that one cancer cell at the time passes a cross-section of the flow channel, positioning the flow channel in a magnetic field that is substantially perpendicular to a longitudinal axis of the flow channel so that magnetically stained cancer cells residing in the flow channel are deflected in the direction of the magnetic field.

The particles to be separated from other particles in a fluid and/or to be separated from the fluid containing the particles may comprise living cells, chromosomes, organelles, beads, biomolecules, such as Deoxyribonucleic acid (DNA), proteins, etc.

Preferably, the flow through the flow channel is a laminar flow so that flow of particles are predictable and easy to control, e.g. with a flow of guiding buffers.

When the flow is laminar, the stream of particles can be positioned as desired within the flow channel, e.g. by controlling flow velocities of the fluid containing particles at the particle inlet of the member and flow velocities of guiding buffers at corresponding inlets.

Preferably, the flow channel is small for the flow through the channel to have a low Reynolds number, e.g. in the range of 0.01–500, such as 0.05–50, preferably 0.1–25. Thereby, inertial effects, which causes turbulence and secondary flows are negligible, viscous effects dominate the dynamics, and mixing is caused only by diffusion. Flow of the sample, which is the fluid containing particles and guiding buffers can be laminated in guided layers through the channel and displacement of particles in the channel is only caused by the external force applied. The Reynolds number referred to is based on the hydraulic diameter of the flow channel, the flow velocity in the axial direction and the fluid density and viscosity, $Re=\rho Dh\mu$ where the hydraulic diameter Dh is defined as four times the cross-sectional area divided by the wetted perimeter.

The illustrated flow channels of the micro flow system have a width ranging from 0.1 to 0.55 mm, preferably ranging from 0.1 to 0.4 mm, in particular ranging from 0.1 to 0.2 mm, and a depth ranging from 0.04 to 0.2 mm, preferably ranging from 0.04 to 0.1. With respect to the lowest cross sectional area of the flow channel, it is preferred that this area is in the range of 0.004 to 0.11 $mm^2$, in particular in the range of 0.004 to 0.02 $mm^2$.

It is believed that any length of the flow channel within the range of 0.1 to 20 mm, preferably 1.0 to 3.5 mm, would lead to satisfactory results.

Preferably, the system is operating with total volumetric flow rates of 0.1 up to 200 µl/min, which gives a flow velocity of 15 mm/min up to 180 mm/min. The average residence time of a particle inside the flow channel, which corresponds to a separation time ranging from 0.1 to 6 sec. The residence time of the sample is defined by the total volumetric flow rate of the system.

The micro flow system may comprise flow rate adjustment means for adjustment of the time the particles reside in the flow channel.

Preferably, the fluid channel is sized so that for efficient separation, particles are displaced 10–30 µm in the flow channel. Thereby, the particle may only be exposed to a field for a very short period of time and thus, continuous separation of particles may be facilitated.

In order to collect the particles, which are deflected in the flow channel, the micro flow system may further comprise second outlet means for discharging particles having been deflected in the flow channel.

The micro flow system may comprise second inlet means for entering a first guiding buffer into the flow channel together with the fluid containing particles. When the flow is laminar, the two fluids flow through the flow channel in parallel abutting each other along a small area extending along a longitudinal axis of the flow channel whereby the cross-section and the path through the flow channel of the flow of the fluid containing particles may be controlled by the first guiding buffer flow. Further, particles in the fluid containing particles may be deflected into the guiding buffer fluid when the two fluids pass the field essentially perpendicular to the longitudinal axis of the flow channel. Furthermore, two (or even more) outlets may be provided at the down stream end of the flow channel for discharging the guiding buffer now containing separated particles and fluid substantially without particles susceptible to the field essentially perpendicular the flow channel, correspondingly.

The micro flow system may further comprise third inlet means for entering a second guiding buffer for improved control of the path of particle flow through the flow channel. By adjustment of the flow velocities of the guiding buffers and the fluid containing particles, the flow within the flow channel of fluid containing particles may be controlled to flow within an essentially cylindrical shaped domain with a longitudinal axis extending substantially parallel to a longitudinal axis of the flow channel and further the position within the flow channel and the diameter of the flow cylinder may be controlled by corresponding adjustments of the volumetric ratio between the flow rate of the fluid containing particles and the flow rate of the guiding buffers.

It is possible to control the cross-sectional area of the domain containing the sample to be a little larger than the cross-sectional area of the particles by adjusting the volumetric flow rates of the sample and of the one or two guiding buffers in such a way that the particles contained in the sample are aligned in a single row of particles. This is a very important feature since it enables individual treatment of each particle and it leads to a sensitive method of sorting particles according to their susceptibility to a field. A sample flow layer thickness less than 1 μm may be achieved.

Preferably, the channel depth is small enough, e.g. below 50 μm, to allow observation of the particles flowing through the channel by a microscope. In an important embodiment of the present invention, the micro flow system comprises a cover, e.g. a transparent or translucent cover, for covering the flow channel. When the cover is transparent or translucent, it will be possible to observe events in the flow channel, e.g. passage of a stained or coloured particle or cell.

The member with the flow channel may be produced from any suitable material, such as silicon, polymers, such as Plexiglas, Teflon, etc., glass, ceramics, metals, such as copper, alumna, stainless steel, etc., etc.

The channel may be provided in the member by any suitable manufacturing process, such as milling, etching, etc.

In a preferred embodiment of the invention, the member is a silicon chip manufactured utilising photolithography and the channel is etched into the silicon chip.

The field may be a magnetic field, an electric field, a gravity field, etc., and any combination of such fields.

A magnetic field may be generated by permanent magnets, such as rare earth magnets, such as samarium-germanium magnets, a mixture of ferromagnetic powder and epoxy, etc., etc., electromagnets, e.g., in silicon integrated electromagnets, etc. The magnets are preferably positioned adjacent to the flow channel so that the magnetic field is substantially perpendicular to a longitudinal axis of the flow channel.

In a preferred embodiment of the invention, the magnets are positioned in and glued to rectangular slots that are etched into a silicon chip. The slots are located adjacent to the separation flow channel. In the example shown in FIG. 1, a permanent magnet or an electromagnet can be received by slots in the micro flow system. The slots are, e.g., 0.5 mm wide, 0.5 mm long and 0.2 mm deep. For generation of a magnetic field, a solid magnetic block, i.e. rare earth magnet can be glued into the slot. Alternatively, a mixture of ferromagnetic powder and epoxy can be injected into the slots to produce a high magnetic field gradient.

The strength of the magnetic field inside the micro flow system may be adjustable. If an electromagnet is used for generation of the magnetic field, the magnitude of the field may be varied by varying the amplitude of the voltage input to the electromagnet. If a permanent magnet generated the magnetic field, the magnitude of the field may be varied by varying the distance between the magnet and the flow channel of the micro flow system.

As already mentioned, the net displacement of a particle in the micro flow system depends on the force applied to it by the field. This can be utilised for separation of a first group of particles of various types in a fluid into a plurality of set of particles; each set comprising a specific type of particles. A micro flow system with e.g. five separation outlets may be used to separate a fluid containing particles into five sets of particles, each set comprising particles that are influenced by the field with a force of a specific magnitude, in the following denoted particles with a specific F-value. Particles with a low F-value are only deflected by a small amount by the field and are discharged from the flow channel through a corresponding outlet port. Particle deflection is increased with increasing F-values whereby such particles are discharged from the flow channel through the corresponding other outlets.

The particles to be separated from other particles in a fluid and/or to be separated from the fluid containing the particles may be magnetically stained to facilitate separation in a magnetic field.

In the present context, the term staining is to be understood in a broad sense. The term is intended to cover any way of marking a particle thereby facilitating detection of the particle. For example a cell may be stained with a fluorescent substance, such as acridin orange, methylene blue, etc, facilitating detection of the stained particles by a fluorescence detector, or, a particle is said to be magnetically stained when it is coupled to a magnetic microbead. The microbead may for example carry a monoclonal or polyclonal antibody on its surface for coupling to an antigene of a cell to be separated utilizing a magnetic field.

In the case where particles have to be detected in a flow channel by optical means, such particles are preferably stained with a chromophoric reagent, or, a fluorescent probe.

An electric field may be generated by electrodes, such as metal electrodes, such as gold electrodes, etc. The electrode may be positioned inside the flow channel, e.g. to introduce electrophoretic forces, e.g. for separation of charged molecules in the fluid, or outside the flow channel e.g. to introduce dielectrophoretic forces, e.g. for separation of particles contained in the flow according to the susceptibility of the particles to the field. Preferably, the electrodes are positioned in such a way that the electric field is essentially perpendicular to a longitudinal axis of the flow channel.

The electric field may be a high frequency field, e.g. a 5 MHz field generated by electrodes positioned inside the flow channel. Living cells positioned in an electric field will be polarized and will be influenced by the field and thus, an alternating field may be used to separate living cells from other particles.

The field generated across the flow channel may be utilised for immobilisation of particles whereby particles may be held in substantially fixed positions within the flow channel for a specific period, e.g. as outlined in FIG. 6, allowing chemical reactions with the particles to take place and/or kinetic measurements on the particles to be performed and/or to bring the particles into contact with different chemical substances or for separating the particles from the sample. The particles may undergo a washing step before removal or reduction of the field redisperses them.

According to a fifth aspect of the invention the above and other objects are fulfilled by a micro flow system for separating particles, comprising a member having a flow channel defined therein for guiding a flow of a fluid containing the particles through the flow channel, inlet means positioned at one end of the flow channel for entering the fluid into the flow channel, field generating means positioned proximate to the other end of the flow channel for generating a field substantially along a longitudinal axis of the flow channel whereby the particles are drawn by the field along the channel and distributed according to their susceptibility to the field and their mobility.

For example, means for generating a magnetic field may be situated at the closed end of a micro flow channel, which at the other end has at least one inlet for entering a sample containing magnetic labelled macromolecules, i.e. ribonucleic acid or proteins. The sample is entered into the channel where the particles are drawn by the magnetic field along the channel and, as by electrophoresis, the particles will be distributed according to their susceptibility to the magnetic field and their mobility. The generated magnetic field is removed after a predetermined time interval and the distribution of particles can then be observed.

According to another embodiment of the invention, the flow through the sort outlet is not continuous but only allowed by a controlling means, e.g. a valve, when a particle with the desired characteristics is detected by a detection means. The particles are sorted using hydrodynamic forces in the sense that the flow is diverged from the ordinary outlet to the sort outlet only when it contains a particle that fulfils certain criteria. The concentration of sorted particles in the flow out of the sort outlet will consequently be high. This is especially an advantage for sample flow with rare occurrence of particles that are searched for. The detection means can be e.g. optical detection means or magnetic detection means e.g. a Hall sensor or means for detecting e.g. electrical or other properties of the particles. The detection means can in an alternative embodiment be used for counting of particles with the desired characteristics as a separate function or in connection with any of the other embodiments described herein.

In yet another embodiment, the field strength is adjustable, e.g. by adjusting the voltage supplied to an electromagnet or to a set of electrodes or by adjusting the distance from a permanent magnet to the flow channel. Particles are in a first operation mode entrapped inside the flow channel by the field at high intensity while at the same time the sort outlet is closed. In a second operation mode, the field is reduced and the sort outlet is open in such a way that the entrapped particles are redispersed and moved out of the sort outlet. Particles that are rare in the sample can by switching between these two operational modes be sorted out in a highly concentrated form. An example of this embodiment is outlined in FIG. 6.

In a further interesting embodiment, the micro flow system according to the invention involves facilities for performing pre-treatment and/or post-treatment of the fluid comprising the particles. These possibilities are outlined in FIGS. 5(f), 7 and 10. As an example, the particles may be treated with a reagent before entering the flow channel, e.g. undergo magnetic or chromophoric staining. Post-treatment may comprise means for collecting or concentrating the deflected particles or means for contacting the deflected particles with one or more reagent(s).

By one possible combination of the pre-treatment and the post-treatment facilities, cells may undergo magnetic staining before entering the flow channel, and after separation the staining may be removed by treatment of the stained cells with a suitable reagent.

It is an important advantage of the present invention that a micro flow system is provided that operates continuously with no requirement for operator intervention.

It is another advantage of the present invention that separation may be performed in one step.

It is still another advantage of the present invention that the particles can be separated in a continuous flow without substantially interfering with the flow itself and that separated particles may be collected at corresponding separated outlets of the flow channel without having to interrupt the flow in the flow channel.

It is another important advantage of the invention that the particles contained in the sample by the adjustment of the flow rate of one or more guiding buffers can be lined up in one row such that the particles can be analysed and sorted individually. This results in a sorting system with the highest sensitivity to the susceptibility of the single particle to the field applied to the sorting channel and a sorting system with the highest resolution of the detection means of the characteristics exhibited by the particles.

It is yet another advantage of the present invention that the micro flow system is easily integrated into other continuous flow systems, such as flow cytometers, flow injection analysis systems, etc.

It is a further advantage of the present invention that particles may be separated into a plurality of groups of particles, e.g. different subpopulations of cells, based on different susceptibility to the field generated across the flow channel of the different groups of particles. This may be obtained by using a multiple outlet micro flow system as outlined in FIG. 5(c).

It is a still further advantage of the present invention that the micro flow system allows observation of particles in the flow channel using a microscope.

It is a still further advantage of the invention that a closed system is provided allowing biohazardous samples, such as samples containing pathogens, to be entered into the system without contaminating the laboratory environment and without causing hazard for operators working with pathogen biomaterials.

It is a still further advantage of the invention that a system with a low shear stress in the flow is provided allowing a gentle treatment of biological samples; e.g. fragile living cells, especially when two guiding buffers are introduced in the channel.

It is a still further advantage of the invention that a high concentration of the sorted particles can be obtained even from samples with rare occurrence of particles that are searched and sorted for.

According to an important aspect of the invention, a new system for immunomagnetic cell separation and manipulation is provided that utilises a silicon based micro fabricated flow chip. The system combines the advantage of flow cytometry and immunomagnetic separation technique. The flow chip will be an important component of a portable micro system for cell sorting and analysis. The flow chip is designed for rapid immunomagnetic cell separation nearly without any pressure drop. Its simple and cheap fabrication and versatile sorting and detection properties offer an alternative to conventional cell separation systems.

It is an advantage of the invention that a micro flow system is provided that is cheap, easy to operate, versatile, simple and portable and that offers the possibility of automation.

A miniaturised flow channel system is provided that utilises the advantageous fluid behaviour in micro systems. The invented system operates continuously. Instead of holding back the magnetisable particles in the separation unit, the particles are deflected into the direction of the magnetic field while passing it continuously. By splitting the fluid flow into two or more outlets, the deflection of the particles can be used for separation of particles into different sets of particles, each of which leaves the flow channel through a specific outlet.

The continuous separation system (CSS) allows efficient enrichment as well as depletion of labelled sample contents of interest. The CSS is designed to fit under a microscope allowing parallel detection of the optical properties of the sample and the control of separation of particles.

An advantage of the geometry of the invented separation flow channel is that a magnetised or electrically charged particle has to be moved only over a distance of 10–30 μm to be separated from the fluid containing particles.

Furthermore, the invention enables isolation of multiple cell or particle subpopulations from a single sample at the same time. The magnitude and direction of the force F on a magnetisable particle, e.g. a magnetically labelled cell, is dependent on the magnitude of the magnetic field and the number of magnetic moments inducible on a labelled cell.

$$F = N*S*\mu B* \text{grad } B$$

where S is the number of Bohr magnetons (μB) per particle and N is the number of particles per cell.

Beads with small S are moving a less distance in lateral direction in relation to the flow through the flow channel than beads with a higher S value. This can be used to separate subpopulation of cells labelled with different magnetisable beads: By splitting the flow channel in various outlet channels cells can be distinguish and separated due to their individual F values.

The drag force on a spherical particle can be found from the particle Reynolds number, based on particle diameter, particle velocity relative to the fluid and fluid viscosity and density. In a flow with a Reynolds number less than 100, the drag force D on the particle can be found from a modified version of Stokes law $$D = 3\pi\mu U d \left(1 + \frac{3}{16}\text{Re}\right)^{\frac{1}{2}}$$

where μ denotes the viscosity of the liquid, U is the relative velocity of the particle and d is the diameter. The numerical value of the parenthesis on the right hand side of the above formula is close to unity for Reynolds numbers less than one why it in that case can be omitted. The magnitude of the drag force on the particles, the force applied to the particle by the field, the distance the particle needs to be moved and the time available for the separation are all important aspects to be considered when a separation process and the device for carrying it out is designed.

An example is given for separation by gravitational means. The effective gravitational force G defined as the gravitational force minus the buoyancy force is found as $$G = (\rho_{particle} - \rho_{liquid})g\frac{\pi}{6}d^3$$

where g is the gravitational constant. For simplicity, a Reynolds number for the particle of less than one is assumed why the drag force D is given in a simple form. These two forces, D and G, are equal when the maximum velocity, the settling velocity $U_\infty$ has been reached. This velocity is found as $$U_\infty = \frac{(\rho_{particle} - \rho_{liquid})gd^2}{18\mu}$$

The velocity to a given time t can be found as $$U(t) = U_\infty \left(1 - e^{-t\frac{g}{U_\infty}}\right)$$

For a particle submerged in water with a diameter of 30 μm and a density of 1.2 times the density of water the settling velocity is $9 \times 10^{-6}$ m/s. The particle will reach 90% of this velocity after $2.1 \times 10^{-5}$ seconds why the transient phase can be neglected. It will take the particle 0.33 seconds to travel a distance of 30 μm, which makes the method reasonable to employ for separation purposes.

While instrumentation in chemistry and biochemistry has become more automated in recent years, the preparation of samples remains a highly laboratory intensive task. The demand is increasing for high throughput, easier to use cost effective analytical devices and assays. Creating this opportunity is e.g. the world-wide effort to sequence the Human Genome, resulting in the development of new DNA diagnostics and therapeutics. Another important trend is the minimisation of health care costs and hospital admissions by testing patients and monitoring therapeutic use in less expensive environments, the so-called point-of-care analysis.

Micro flow devices containing arrays of nucleic acid hybridisation sites, known as genosensors, are being developed for a variety of uses in genomic analysis. A great deal of the overall genosensor development effort involves optimisation of experimental conditions in the actual use of genosensors.

Another embodiment of the invention is dealing with a low-tech form of genosensor and immunosensor technology, involving arrays of oligonucleotides on a microchip, which can be used to define optimal operating conditions and to develop applications of hybridisation arrays in genome mapping and sequencing. The genosensor array is placed in a micro flow channel system allowing an operation in a flow-through mode. Thus several steps of microliquid handling, e.g. washing and staining steps, reagent addition, can be integrated as an automated routine procedure. Additionally, micro flow devices containing arrays of antibody/antigen sites, known as immunosensors, can be designed in the same way. The system could be used for combinatorial screening (high-throughput screening) and pharmacokinetic studies.

According to a sixth aspect of the invention the above and other objects are fulfilled by a micro flow system for analysing components of a fluid, comprising a member having a flow channel defined therein for guiding a flow of a fluid through the flow channel, first inlet means for entering particles into the flow channel, first outlet means for discharging of fluid from the flow channel and a plurality of assay sites located in the flow channel and comprising immobilised reagents whereby the fluid may be analyzed for a plurality of components while residing in the flow channel.

The system may further comprise field generating means positioned proximate to at least some of the assay sites for generation of a field proximate to the corresponding assay site whereby reagents residing in the flow channel and being susceptible to the field when generated at a selected assay site are attracted to and immobilised at the selected assay site, or, are rejected from the selected assay site.

In an embodiment of the invention, the member comprises a plurality of flow channels arranged in parallel or in series and each of which has assay sites whereby the fluid containing particles is brought into contact with a large number of assay sites.

According to a seventh aspect of the invention, a method of analysing components of a fluid is provided, comprising the steps of entering a fluid containing the particles into a flow channel and allowing the fluid to flow in the channel, the channel having a plurality of assay sites, each of which comprises immobilised reagents whereby the fluid can be analyzed for a plurality of components while residing in the channel.

According to a eighth aspect of the invention, a method of forming assay sites comprising immobilised reagents in a flow channel is provided, the method comprising the steps of preparing selected surfaces of the assay sites for immobilisation of selected reagents, dispensing a selected reagent proximate to a corresponding selected assay site, and generating a field proximate to the selected site whereby the reagent is attracted towards and brought into contact with the surface of the selected assay site by the field generated and is immobilised upon contact with the surface.

Thus, the micro flow system of the previous section with a flow channel with assay sites may further comprise field generating means positioned proximate to at least some of the areas adapted to comprise immobilised reagents, each field generating means generating a field proximate to the corresponding area whereby reagents entering the flow channel and being susceptible to the field generated at the area are attracted to and immobilised at the area or are rejected from the area. Alternatively, the width of the channel of the micro flow system can be extended to accommodate a two-dimensional grid of areas to comprise immobilised reagents with fields generating means positioned proximate to at least some of these areas. In another embodiment the micro flow system for analysing a sample with a large number of reagents simultaneously may consist of an array comprising a number of parallel channels each with a plurality of areas adapted to comprise immobilised reagents located in the flow channels and further comprising field generating means to generate a field proximate to the areas whereby reagents being susceptible to the field are immobilised at the area. The field generating means may be e.g. permanent magnets, electrodes or electromagnets.

The devices with assay sites enable rapid manipulation, detection, and analysis of macromolecules, particles and cells in biologic or chemical samples in that a plurality of tests can be performed on the same microchip. According to the invention, micro flow systems and molecular biology are combined.

BRIEF DESCRIPTION OF THE DRAWINGS

Exemplary embodiments of the invention will now be described with reference to the accompanying drawings in which.

DETAILED DESCRIPTION OF THE DRAWINGS

According to a preferred embodiment of the invention, magnetically stained particles, e.g cells labelled immunologically with magnetic particles, such as antibody-coupled magnetic beads, are separated from non-magnetic particles, i.e. non-labelled cells, by exposing the particles to a magnetic field generated with a permanent or an electromagnet. Positive or negative selection methods may be employed.

By positive cell separation, cells of a specific cell type are separated and isolated from a heterogeneous mixture of cells.

Figure 1:
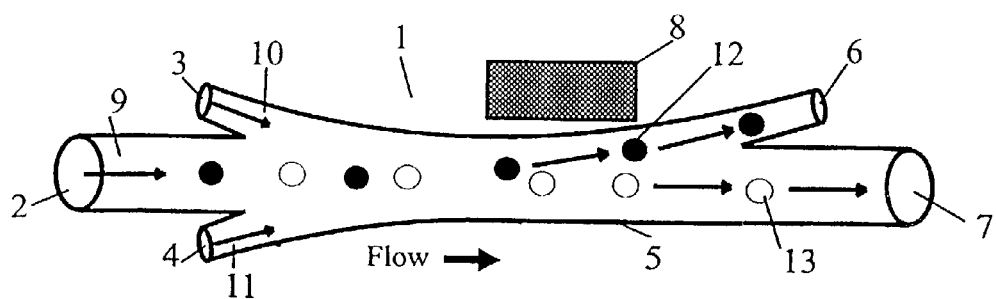
FIG. 1 illustrates the operation of particle separation according to the present invention.

FIG. 1 illustrates the principle of the separation method according to the invention. A micro flow system 1 is shown having three inlet and two outlet ports. The sample 9 containing particles enters the separation flow channel 5 through a central inlet port 2 and is continuously guided through the separation flow channel 5 of the micro flow system 1 by two guiding buffers 10 and 11, each of which enters the separation flow channel through inlet ports 3 and 4, respectively. A field generating means comprising a magnet 8 is located adjacent to the flow channel 5 and generates a magnetic field across the flow channel 5. When the sample 9 containing particles passes the magnetic field, magnetically stained particles 12 are drawn into the guiding buffer 10 and leave the flow channel 5 together with the guiding buffer 10 through the sort outlet 6 while non-labelled cells 13 which are not influenced by the magnetic force remain in the fluid 9 leaving the flow channel 5 through the waste outlet 7.

Due to the small channel dimensions, the flow is laminar with negligible influence of inertial forces. Mixing of the sample flow and the guiding buffers is not detectable since the contact area is small and the contact time is reduced to a subsecond range. The thickness of the sample flow can be precisely adjusted by variation of the flow rate of the two guiding buffers. This enables the adjustment and optimisation of the magnetic micro flow system for various cell types and sizes. The volume flow of the sample and the two guiding buffers are adjusted so that the particles in the sample are lined up into a single stream of particles.

The magnetic field in the micro flow channel operates as an extremely sensitive filter for magnetic particles, e.g. cells. Cells labelled with superparamagnetic beads (e.g. MACS, Dynal) are magnetised and attracted by the magnetic field whereby the flow of magnetised particles is deflected into the sort outlet. The short residence time of the fluids in the flow channel and the low Reynolds numbers of the flow in the flow channel minimise the influence of gravity compared to the influence of the magnetic force.

Figure 2:
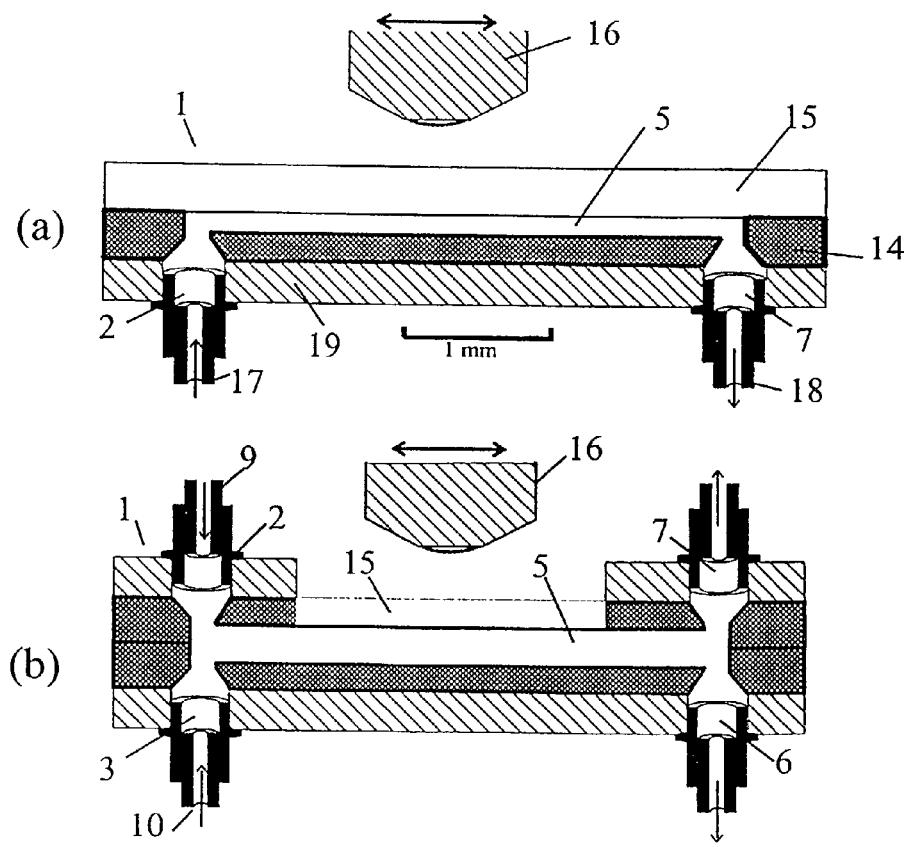
FIG. 2 shows a cross-sectional view of a separation flow channel according to the present invention. (a) shows the main embodiment and (b) shows a cross-sectional view of a separation flow channel for gravitational separation.

FIG. 2 shows a cross-sectional view of two variants of the micro flow system 1 manufactured utilising semiconductor technology. The micro flow system may be manufactured in any suitable material such as polymers, glass, semiconductors, such as silicium, germanium, gallium arsenate, etc., etc.

The first micro flow system (a) shown is a 3-layer sandwich. The central layer 14 is a silicon wafer having a flow channel 5 etched into it. The silicon wafer 14 is covered with a transparent plate 15, such as a glass plate, having a thickness of, e.g., 0.16 mm. Fluids inside the flow channel 5 may be observed through the glass plate 15, e.g. utilising a microscope 16 (detection means). The fluid inlet 2 and outlet 7 are connected to tubings 17, 18, e.g. fused silica capillary or Teflon tubings, for entering fluids into or discharging fluids from the flow channel 5. Buffer inlets 3 and 4 and the outlet 6 for the separated particles are not shown. The bottom plate 19, e.g. made of plastic, facilitates mounting of the tubings 17, 18.

A modified version (b) of the micro channel system for separation was designed with gravitation as the force field, thus sorting particles due to their density and/or diffusion constant, the latter mainly being controlled by the shape and size of the particles. The system is during operation positioned with the flow plane substantially perpendicular to the direction of the force of gravity. As illustrated in FIG. 2(b), this embodiment of a micro flow system 1 has a sample inlet port 2 and an outlet port 7 located above the micro channel 5 and a buffer inlet port 3 and an outlet port 6 located below the micro channel 5. The sample containing particles 9 enters the separation flow channel through inlet port 2, and a guiding buffer 10 enters the separation flow channel 5 through inlet port 3. In this way, two laminated layers of fluid extending along the horizontal plane are created continuously flowing through the separation flow channel 5 of the micro flow system 1. Particles move from the particle containing layer to the guiding buffer layer by sedimentation. When the sample containing particles 9 passes the flow channel 5, particles with certain density and size properties are drawn into the guiding buffer 10 by the gravitational force and leave the flow channel 5 together with the guiding buffer 10 through the outlet port 6 while particles which are less susceptible to the gravitational field remain in the sample 9 leaving the flow channel 5 through the waste outlet 7. The vertical displacement of a specific particle in the sample is given by its density and diffusion constant and the contact time of the sample layer with the guiding buffer layer. The contact time is defined by the total flow rate of the fluids passing through the micro systems 1 and the length of the micro channel 5. The system can be adjusted such that a desirable or appropriate specimen can be withdrawn and separated from the sample flow due to their density and/or diffusion properties by adjusting the volumetric flow rates of the guiding buffer and particle containing sample.

Alternatively, the micro flow system may comprise two further inlet ports for entering a second and a third guiding buffer into the micro channel 5, where the two further inlet ports are positioned above the micro channel, one on each side of the sample inlet port 2. The flow rates of the sample and the second and third guiding buffers may be adjusted so that the particles contained in the sample are lined up in a single line.

Characteristic features of an exemplary embodiment of a micro flow system according to the invention, e.g. as shown in FIGS. 1 and 2, is shown in Table 1.

TABLE 1

| Characteristics, micro flow system | |
|---|---|
| Manufacturing method | Material: Silicium Oxide, $SiO_2$ |
| | Photo-lithography |
| | Wet-chemical etching |
| Flow Channel | |
| Cross sectional area | 0.1–0.55 mm width × 0.04–0.2 mm depth |
| Length | 1.0–200 mm |
| Total flow rate [µl/min] | 1–200 |
| Flow velocity [mm/min] | 15–180 |
| Reynolds number | 0.1–20 |
| Separation time | 0.1 sec–6.0 sec [2 µl/min] |
| Magnet | |
| Permanent Magnet | |
| Rare Earth Samarium-Germanium | 0.5 × 0.5 × 0.2 mm |
| Electromagnet | |
| Holding Magnet | 25 mm 12 V D.C. RS |

Figure 3:
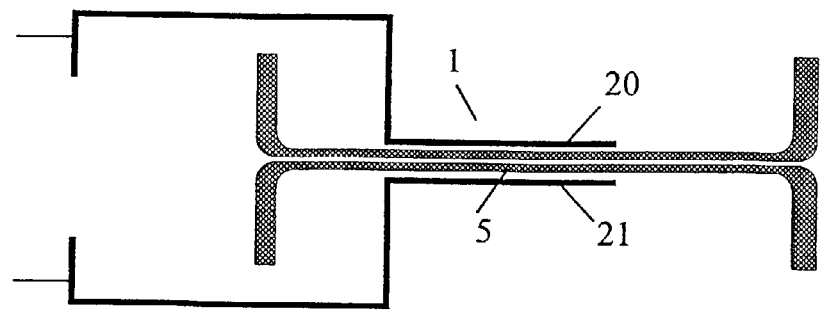
FIG. 3 shows a micro flow system with electrodes as field generating means.

FIG. 3 shows a micro flow system 1 utilising electrodes 20, 21 to generate an electric field across the flow channel 5. The electrodes 20, 21 may introduce dielectrophoretic or electrophoretic forces utilised for particle separation. For electrophoretic separation to take place, gold electrodes may be positioned at the inside of the walls of the flow channel 5. By applying a voltage across the electrodes, an electrical field is generated substantially perpendicular to a longitudinal axis of the flow channel. The electrical field cause deflection of charged particles or molecules in the flow channel 5 whereby electrically charged particles can be deflected away from the sample containing particles flowing in the micro flow channel and into a guiding buffer also flowing in the flow channel and abutting the sample containing particles in the micro flow channel.

Figure 4:
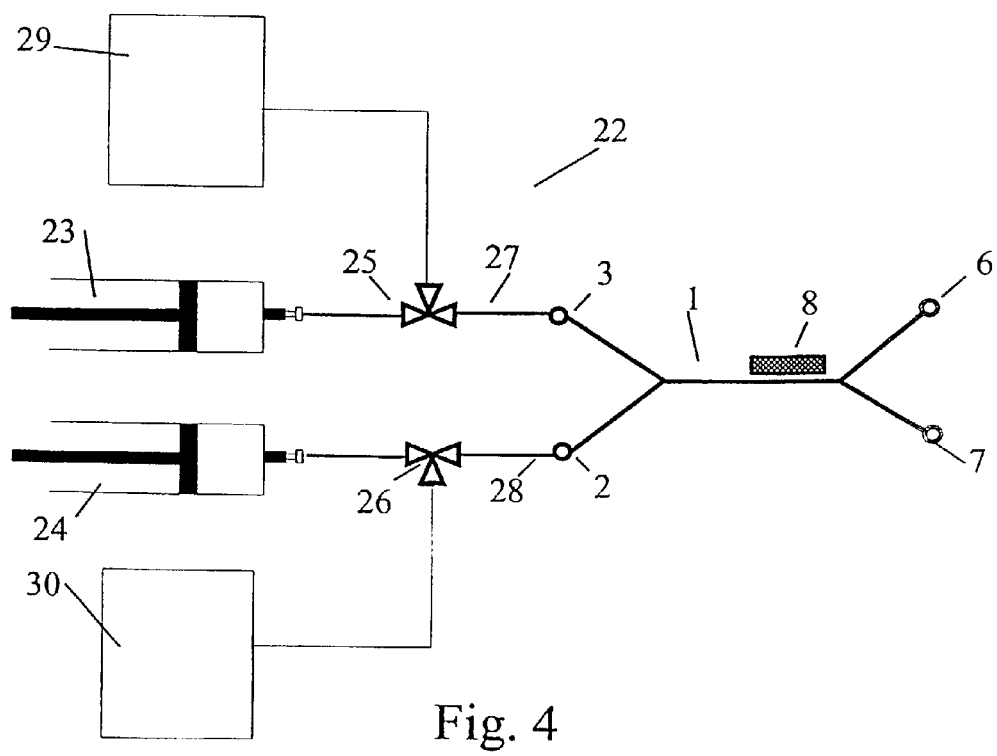
FIG. 4 shows a flow diagram of a magnetic particle separation apparatus according to the present invention.

FIG. 4 shows a micro flow apparatus 22 including a micro flow system 1 as shown in FIGS. 1 and 2. The micro flow system 1 has two inlets 2, 3 and two outlets 6, 7, two syringe pumps 23, 24, two 3-way control valves 25, 26 and capillary tubings 27, 28. The capillary tubings 27, 28 are used for interconnecting the two syringe pumps 23, 24 with the inlets 3, 2, respectively, of the micro flow system 1.

Conventional syringe pumps with means, e.g. steppingmotors (not shown), to move the pistons at a predetermined speed have been utilised for generating a continuous flow of the guiding buffer through the inlet tube 27 and a continuous flow of the sample through the inlet tube 28. The system can be operated in a first loading mode where the two 3-way control valves 25, 26 open for flow between the syringe pumps 23, 24 and the buffer reservoir 29 and the sample reservoir 30, respectively, and the syringe pumps 23, 24 are loaded with buffer and sample from the reservoirs 29, 30, respectively. In a consecutive second operational mode the two 3-way valves 25, 26 open for flow between the syringe pumps 23, 24 and the capillary tubing 27 to the buffer inlet 3 and the capillary tubing 28 to the sample inlet 2 of the micro flow system 1, respectively. The syringe pumps are in this second operational mode controlled to generate a predetermined volumetric flow rate through the micro flow system 1.

Figure 5:
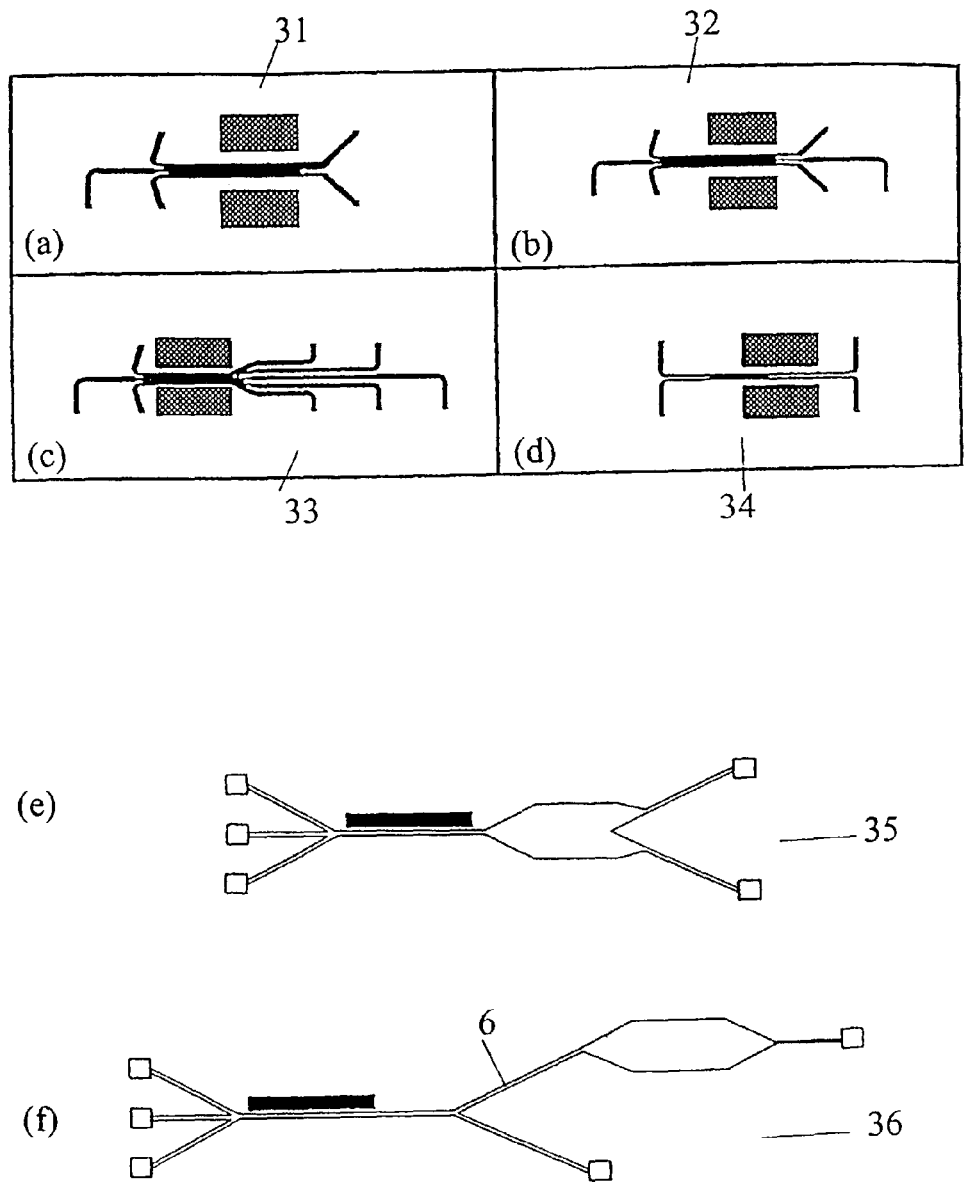
FIG. 5 shows flow diagrams of various embodiments of the present invention. (a)–(d) show embodiments with various numbers of inlets and outlets, and (e) shows an embodiment with an enlarged separation chamber, and (f) shows an embodiment with an enlarged chamber for collecting separated particles.

FIG. 5 illustrates various micro flow systems 31, 32, 33, 34, 35, and 36 having flow channels of different geometries, illustrating different embodiments of the invention. Micro flow systems with two or three inlet ports and two, three or five outlet ports, respectively, are shown in FIGS. 5(a)–(d). The system shown in 5(a) with inlet ports for sample and two guiding buffers, respectively, and sort outlet port and waste outlet port is similar to the system shown in FIG. 1. FIGS. 5(b) and (c) show systems with multiple outlet ports, three and five, respectively, whereto particles can be sorted and leave the flow channel through according to their susceptibility to the applied field. A simple system with two inlet and two outlet ports are shown in FIG. 5(d) similar to the one in FIG. 2(b) that is used for gravitational sorting. A micro flow system with a separation channel equipped with a magnet where the width of the separation channel is enlarged before the bifurcation in a sort outlet and a waste outlet is shown in FIG. 5(e). According to the behaviour of liquids in a flow channel, the size of the cross-sectional area occupied by the sample flow is proportional to the width of the separation channel. According to this, the transversal distance between two particles A and B is increased proportional to the increase of the width of the separation channel. A larger distance between particles, which are to be separated, yields a higher selectivity of the mechanical separation. FIG. 5(f) shows a micro flow system where the width of the outlet channel 6 is increased to form a chamber where the sorted particles are collected for further processing or analysis, e.g. detection, staining, destaining or cultivation.

Figure 6:
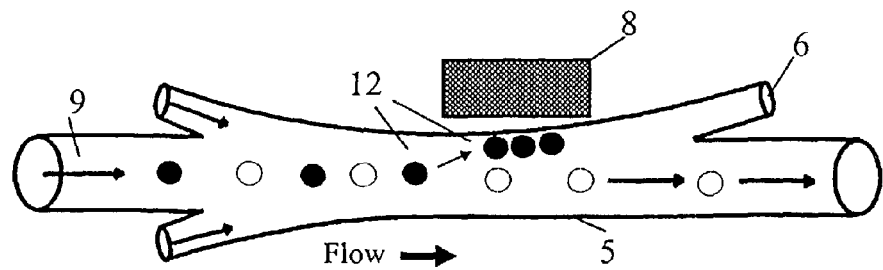
FIG. 6 illustrates entrapment of magnetic particles in a flow channel.

FIG. 6 illustrates a system in which particles are entrapped inside the micro flow channel 5 for a desired period using the electromagnet-equipped apparatus. In this case, the magnetic field is adjusted so that magnetic particles 12 are drawn to the inner wall of the micro flow channel 5 close to the electromagnet 8. Upon removal of the current to the electromagnet 8 the particles 12 are redispersed and are rapidly moved to the sorting outlet port 6. This 2-step sorting procedure is an alternative to the continuous sorting procedure that is particularly useful in sorting of extremely rare events where dilution of the sorted cell fraction could be a problem. The sorting outlet port 6 may be closed when the current to the electromagnet 8 is turned on and is open when the current to the electromagnet 8 is turned off. The figure shows magnetic particles 12 in the process of being withdrawn from a continuous sample flow 9. The magnetic particles 12 are attracted by the magnetic field and withdrawn from the sample flow 9 by precipitation at the inner wall of the micro flow channel 5 proximate to the electromagnet 8. When the current supplied to the electromagnet 8 is turned off, the magnetic particles 12 are released into the flow again. The separation flow channel may not have a sort outlet, instead a buffer may enter the micro flow channel 5 after the sample and the entrapped particles may be released by removing the current supplied to the electromagnet 8.

Figure 7:
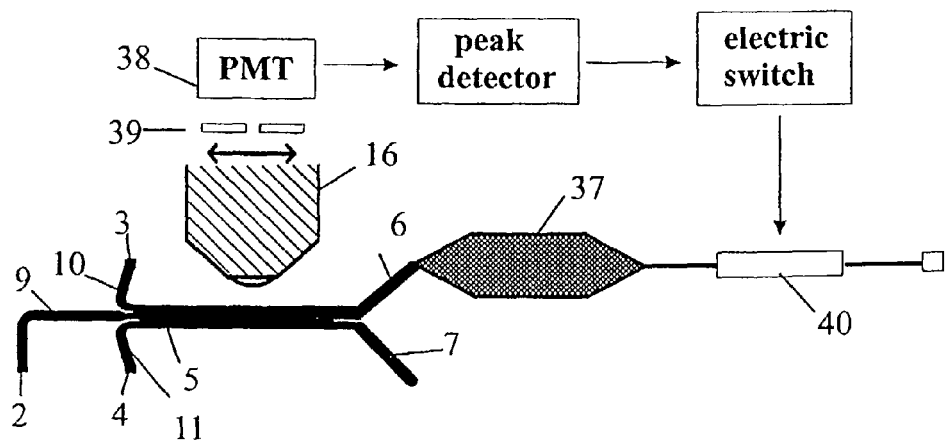
FIG. 7 shows a flow diagram for optical detection and hydrodynamic separation using a blocking valve.

FIG. 7 illustrates another embodiment of the present invention for separation of particles fulfilling certain criteria from the sample 9 by hydrodynamic force. The apparatus comprises a 2-way valve 40 and a micro flow system having a separation flow channel 5 with three inlets 2, 3, 4, two outlets 6, 7 and a collecting chamber 37. The sample 9 containing particles enters the separation flow channel 5 through a central inlet port 2 and is continuously guided through the separation flow channel 5 of the micro flow system by two guiding buffers 10 and 11, each of which enters the separation flow channel 5 through inlet ports 3 and 4, correspondingly. The sample 9 is monitored utilising a microscope objective 16. The apparatus has control means 38 for controlling the two-way valve 40. The control means comprises monitoring means having an optical detection means, e.g. a photomultiplier system (PMT), a CCD camera/chip or a photo diode, optically connected to the microscope objective 16. The objective 16 is focused on the measuring volume, which is located inside the flow channel 5. The size of the measuring volume is defined by a pinhole or slit 39 positioned in front of the optical detector and by the magnification of the objective 16. The 2-way valve 40, e.g. a piezoelectric drop-on-demand inkjet printing valve, is connecting the collecting chamber 37 to the sort outlet 6. The flow restriction of the waste outlet channel 7 is much higher than the flow restriction of the sort outlet channel. This can be achieved by attaching a flow restrictor (not shown) to the waste outlet channel 7. Thus, if the 2-way valve 40 is open the sample 9 containing particles is deflected towards the sort outlet 6. The collecting chamber 37 is used to collect and capture the sorted particles for post-analysis. Other particles continue to flow out through the waste outlet 7.

Particles are physically separated using hydrodynamic forces according to optical measurements on each particle. The photomultiplier (PMT) signal generated when a particle resides in the measuring volume is transmitted to a pulseheight analyser also comprised within the control means 38. A selection circuit provides an activating signal whenever a specific particle exhibits photometric properties of a predetermined type. If the PMT signal for a specific particle indicates that the particle is of a specific type an actuation pulse is produced. The valve 40 opens at the actuation pulse, causing the liquid containing the specific particle to flow through the sort outlet 6 and to be captured inside the collecting chamber 37. The duration of the actuation pulse is made sufficiently long for the desired particle to be transported into the collecting chamber 37. For light excitation several sources can be used, e.g. laser, tungsten lamp, photo diode. For bundling of the light, a fibre optic cable, a photo lens, an objective or a light microscope can be used. Various optical detection methods, e.g. fluorescence, absorbency, can be used.

The micro flow system may be positioned on a movable table so that the micro flow system may be moved into selected positions relative to the microscope whereby an appropriate volume of the micro flow channel may be moved into the measurement volume of the apparatus.

During or after sorting, the captured sample can be analysed again, using e.g. a microscope. When the valve 40 is closed, particles are entrapped inside the collecting chamber 37 and can be observed for a desired period. A desired liquid or reagent for washing, cultivation or staining of particles or cells may be entered into the collecting chamber 37. After the separation process, the particles may be withdrawn by flushing the collecting chamber 37 with an appropriate buffer entering the micro flow system through one of the inlets 2, 3, 4.

The sorting apparatus was designed to achieve a minimal dilution of the separated sample fraction. Hydrodynamic separation of particles can be performed due to the optical, electrical, magnetic and/or other properties of the particle-containing sample.

An example of an optical and mechanical arrangement of the apparatus based on fluorescence detection is illustrated schematically in FIG. 7. The sample 9, e.g. particle suspension, is guided through the separation channel 5 by two guiding buffers 10, 11 so that the particles contained in the sample 9 are lined up in a single stream flowing in a plane perpendicular to the optical axis of the objective 16. The flow is illuminated with a mercury arc lamp passing excitation filters for e.g. fluorescein measurement. A dicroic mirror reflects the excitation light to the sorting chip via e.g. a 20× microscope objective 16. The fluorescence light emission is collected by the same objective 16 passing a dicroic mirror. Behind the mirror, a slit 39 works as field stop limiting the detection area to a small stripe. Each particle passing the objective 16 is generating a short signal from the photomultiplier that is optically connected to the objective 16. The photomultiplier signal is amplified and transmitted to a peak detector.

The actuation frequency of the valve 40 used in this device is 1500 Hz which corresponds to a minimal actuation time of 0.6 msec.

Figure 8:
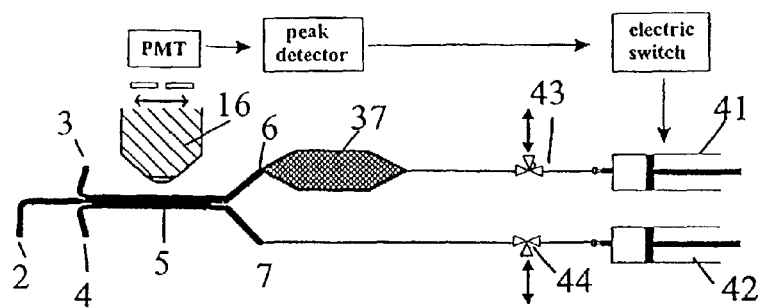
FIG. 8 shows a flow diagram for optical detection and hydrodynamic separation using syringe pumps.

FIG. 8 illustrates an alternative embodiment of the separation apparatus shown in FIG. 7 with a separation flow channel 5 having three inlets 2, 3, 4 and two outlets 6, 7. The sample containing particles enters the separation flow channel 5 through the centre inlet port 2 and two guiding buffers enters the channel 5 through the other two inlet ports 3, 4, respectively. Flow speed adjustment means comprising stepper motor driven syringe pumps 41, 42 are connected to the two outlet ports 6, 7, respectively. The syringe pumps 41, 42 suck the sample and buffer via inlet 2, 3 and 4, respectively, through the separation flow channel 5. The cells are monitored at the optical axis of the microscope objective 16 and flow to the separation junction. The guiding buffers and the sample containing unselected cells flow out into the waste outlet syringe pump 42. If a specific cell has optical properties causing an actuation pulse, the stepper motor of the pump 41 at the sort outlet is actuated and the stepper motor of the pump 42 at the waste outlet is stopped causing the liquids to flow to the sort outlet 6. The period the pump 41 at the sort outlet is switched on, respectively the pump 42 at the waste outlet is switched off is made sufficiently long to ensure that the desired cell has entered into the collecting chamber 37. When one of or both syringe pumps 41, 42 after some operation time need to be emptied, the 3-way valves 43, 44 are switched from their normal operation position where they open for flow from the separation flow channel 5 to the syringe pumps 41, 42, respectively, into a position where the 3-way valves 43, 44 open for flow between the syringe pumps 41, 42 and a waste container (not shown) and where the stepper motors driving the syringe pumps 41, 42 are operated in the reverse direction of the normal operation direction to empty the syringe pumps 41, 42.

Figure 9:
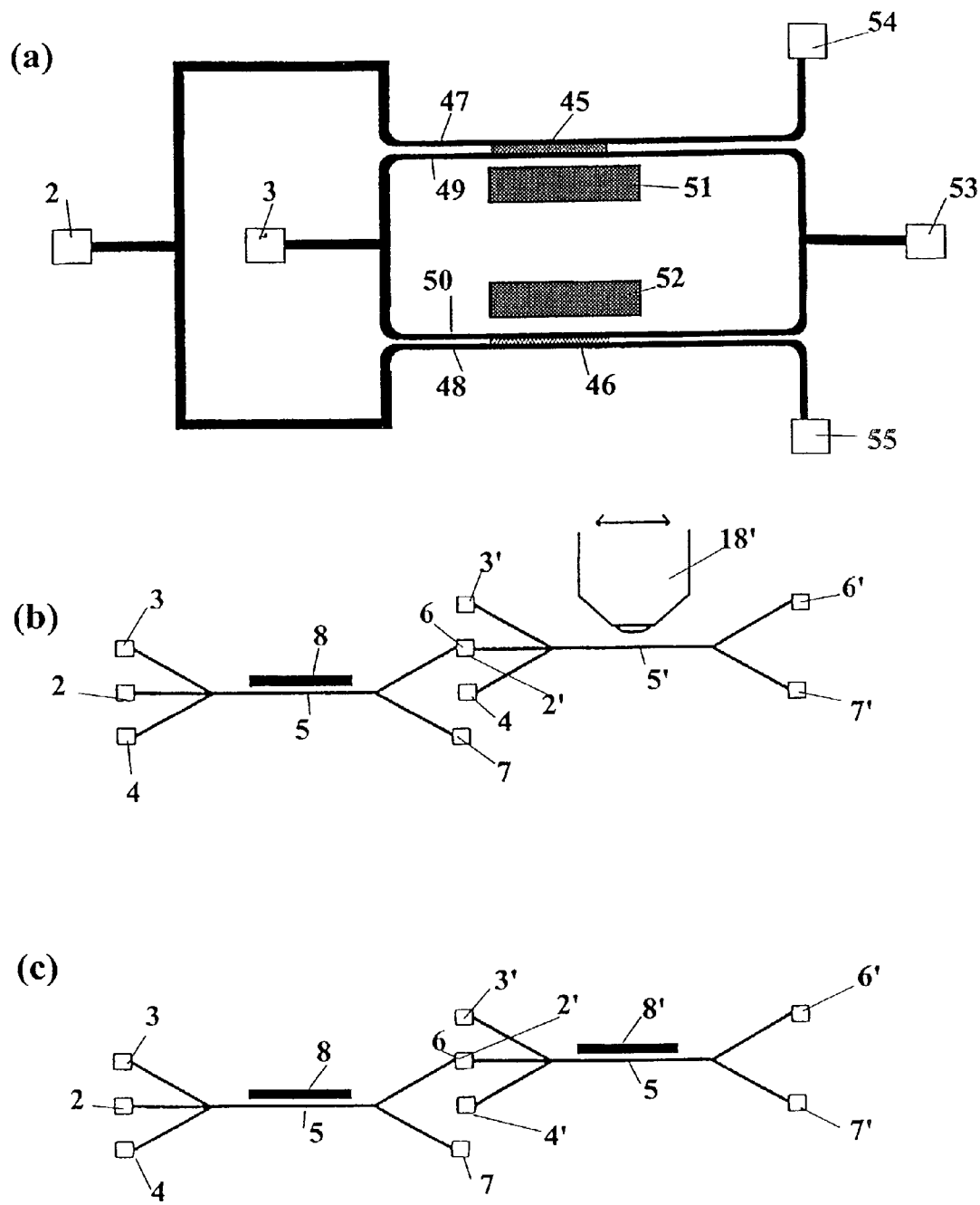
FIG. 9 shows a flow diagram of two flow channels coupled in parallel (a) and in sequence (b) and (c)

FIG. 9(*a*) shows two flow channels 45, 46 operating in parallel. The sample containing particles enters the flow channels 45, 46 through inlet ports 47, 48, respectively. The guiding buffer enters the flow channels through the inlet ports 49, 50, respectively. In the flow channels 45, 46, particles susceptible to the magnetic field generated by magnets 51, 52, respectively, are deflected from the sample containing particles into the corresponding guiding buffer and flow thereafter through the sort outlet 53. The remaining part of the sample leave the flow channels 45, 46 through the waste outlets 54, 55, respectively. Separation is increased by using a plurality of flow channels coupled in parallel.

FIGS. 9(*b*) and (*c*) shows examples of combinations of micro flow systems for magnetic, hydrodynamic or gravitational separation. In FIG. 9(*b*), particles are first separated from a sample in a magnetic separation channel, where after the sorted particles are subjected to a hydrodynamic separation due to the optical properties of the particles. Thus, it is possible to analyse and separate particles from a sample based on both optical and magnetic properties of the particles or to another combination of properties or characteristics. In FIG. 9(*c*), two magnetic separation channels are coupled in series in order to obtain a highly purified product.

Figure 10:
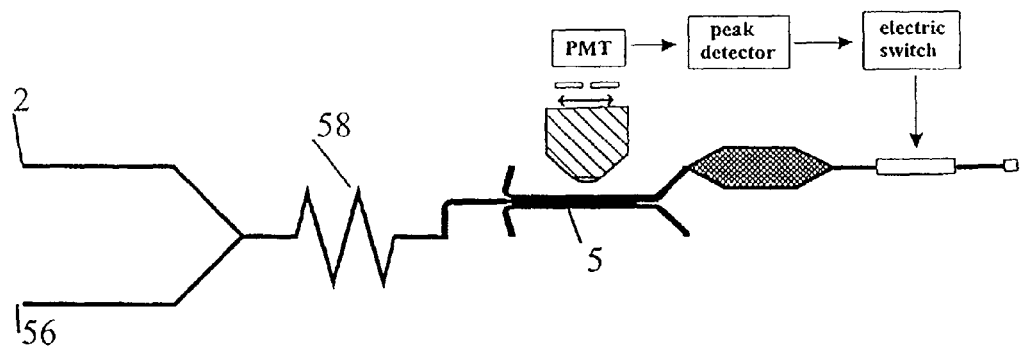
FIG. 10 illustrates the principle of introducing a pretreatment facility in the member comprising the micro flow system, here further combined with a post-treatment facility or a hydrodynamic separation facility.
Figure 10:
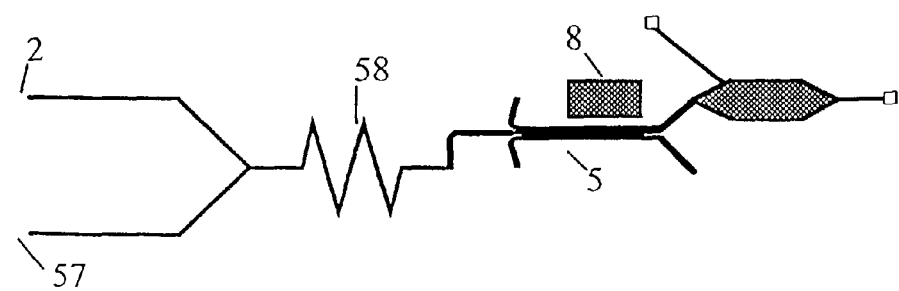

FIG. 10 illustrates examples of micro flow systems having means for automated labelling of particles with fluorescence or magnetic probes. The system may be combined with post-treatment means for removal of the probes or for other treatment of the sorted particles. The system contains a micro flow system containing channels 56, 57 for addition of liquids to the sample, e.g. reagents for cell lysis or staining, a channel 58 for incubation and cultivation or storage of the sample for further processing and a separation channel 5. A sample is introduced into the micro flow system via an inlet 2 and one or more reagents can be added continuously to the sample, which is transported into the incubation channel 58. A simple micro flow structure was constructed for sample pre-treatment. Preferably, the flow rates are managed by computer-controlled syringe pumps. The incubation period between mixing and analysis of the sample is given by the volumetric flow rate of the syringe pumps and the cross-sectional area and length of the incubation channel.

Figure 11:
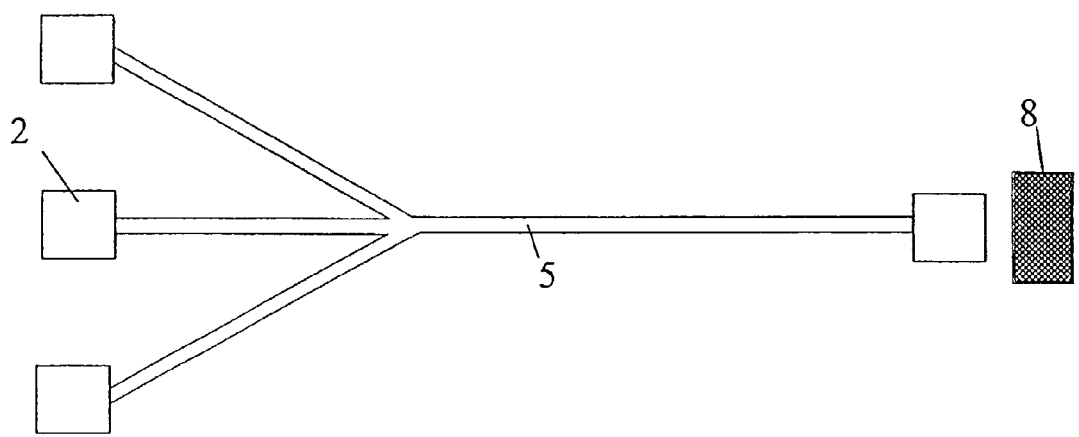
FIG. 11 shows a flow channel for magnetophoresis.

FIG. 11 shows a micro flow system for magnetic separation of macromolecules, i.e. ribonucleic acid or proteins from a sample. Magnetic beads labelled with a fluorescence dye and a probe, specific for i.e. DNA are added to the sample which is then incubated. This sample is entered via inlet port 2 into the separation chamber 5 and the particles are drawn by the field generated by the magnet 8 along the separation channel 5 due to their mobility. After a defined period, the magnetic field is removed and the fluorescence banding can be observed under a microscope. By running standards of known size, it is possible to calibrate the system and to separate particles of e.g. DNA due to their size and shape, similar to electrophoresis.

Figure 12:
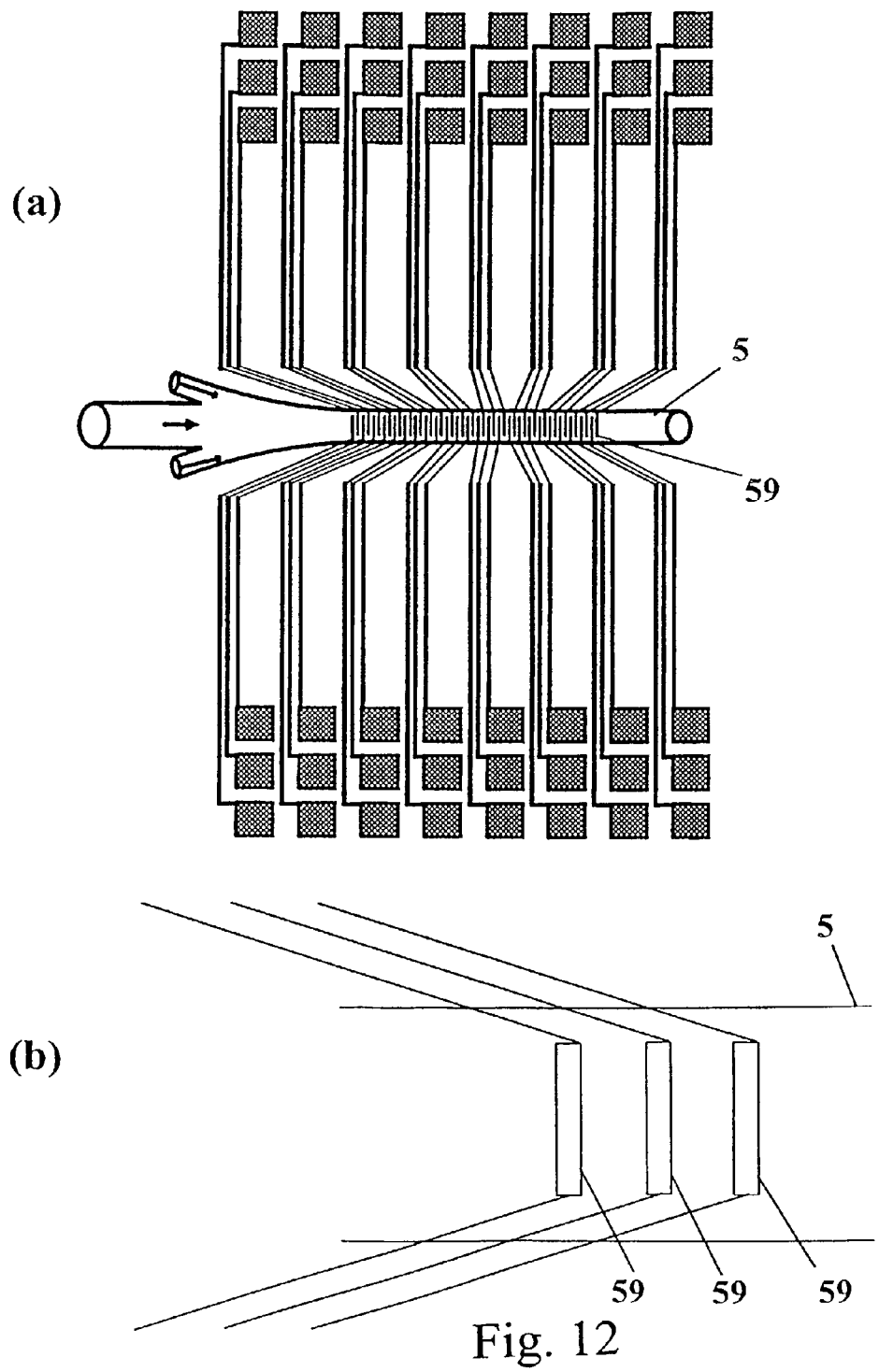
FIG. 12 shows a flow channel having a serial array of assay sites equipped with electrodes to immobilise probes.

FIG. 12(*a*) with details in FIG. 12(*b*) shows a serial sensor array. A micro flow channel 5 has a plurality of assay sites, each equipped with field generating means 59 that may be individually turned on and off. The flow channel 5 shown has rectangular electrodes 59 positioned in small grooves at the bottom wall of the flow channel 5. A voltage can be applied selectively to each electrode 59. Various probes, receptors, indicators, etc. may be attracted to and immobilised at selected electrodes 59 by applying a voltage to the selected electrodes 59 while a fluid containing the corresponding probes, receptors, indicators, etc. resides in the flow channel 5. Preparation of the multiple assay sites may be accomplished by sequentially loading each assay site with a specific probe. Voltage is applied to one or more specific electrodes in the micro flow channel 5, and a fluid containing a specific probe, reagent or indicator, etc. is entered into the micro flow channel 5 where the probes etc. will be attracted to the electrodes to 59 which the voltage is applied. Subsequently, the voltage is turned off. Then, a voltage is applied to the next electrode 59 and the next fluid containing a specific probe etc. is entered into the micro flow channel 5. Thus, various assay sites each containing a specific probe, reagent, or indicator can be created. Antibodies, fluorescence molecules, DNA, RNA and protein dyes are examples of probes.

As an alternative to the electrodes 59, magnetic force can be selectively applied to the assay sites with an array of electromagnets positioned at or near the surface of the micro flow channel 5 to immobilise probes etc. that have magnetic properties to desired assay sites. Alternatively, a photoactivation process can be used for covalent coupling of molecules or particles to the surface of the channel 5 at the assay site.

One example of a probe is DNA, which has an overall negative charge, drawn to the electrode 59 surface by a positive bias, another example is DNA-coated magnetic particles that are drawn to the surface of micro flow channel 5 by magnetic means.

By modification or coating of the surface of the micro flow 5 channel and/or the electrodes 59 or magnets, specific chemical and mechanical properties can be created. To increase the binding forces of the probe, the surface may be coated with a specific layer or matrix, e.g. a polymer such as urethane or a reactive chemical group. When the current to the selected electrode or electromagnet is switched off the probe remains on the surface e.g. by absorption. Thus, an encapsulation or immobilization of the molecule is achieved.

Thus, a field generated at selected assay sites across the flow channel 5 may be utilized for immobilization of particles, such as biomolecules, whereby these may be held in substantially fixed positions within the flow channel permanently or for a specific period of time allowing chemical reactions between the particles and an entered reagent to take place and/or kinetic measurements on the particles to be performed and/or the particles to be brought into contact with different chemical substances. For analysis of the reactions in the micro flow system, optical detection means, e.g. a microscope, may be used.

It is an important advantage of the device that a number of assays can be performed in a single device. During operation of the device, various processing steps, such as e.g. washing steps, and reagent addition, etc., may be performed.

Figure 13:
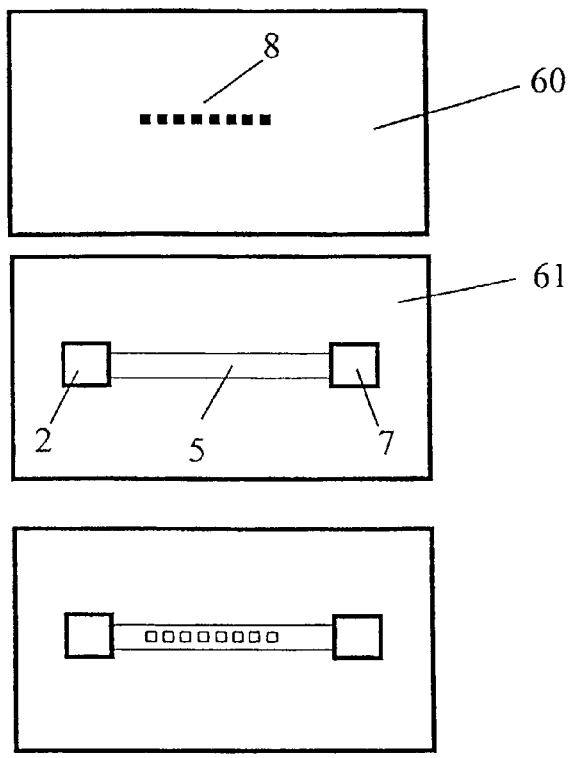
FIG. 13 shows a flow channel having a serial array of assay sites equipped with magnets to immobilise probes.
Figure 13:
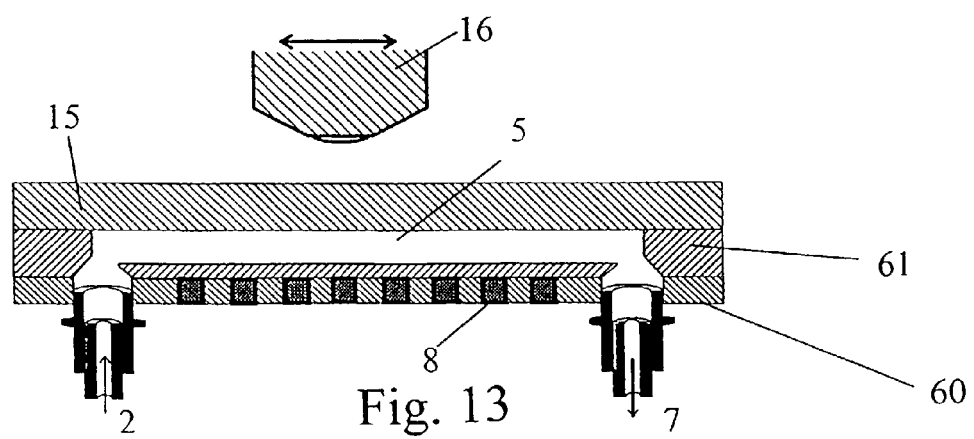

FIG. 13 shows a micro flow device with a flow channel 5 and with a serial array of assay sites and permanent magnets 8 positioned on a separate cartridge 60. A second cartridge 61 has a flow channel 5 with an inlet 2 and an outlet 7. The cartridge 60 carrying the magnets 8 can be positioned exactly below the second cartridge 61 so the magnets 8 are accurately positioned below the assay sites in the flow channel 5 as shown in the figure below cartridge 61.

Probes to be immobilised at a specific assay site utilising a magnetic field, as described in FIG. 12 or FIG. 13, may be positioned at the desired assay site by a method comprising the steps of positioning a defined volume of the liquid containing the magnetic probe or reagent using e.g. inkjet based dispenser technology, within a specific volume of the flow channel 5 right over one of the permanent magnets 8 for immobilization of the magnetic probe or reagent in an assay site at the surface of the flow channel 5. The method may be repeated for various probes to be immobilised at various assay sites, respectively After the immobilization, the cartridge 61 containing the flow channel 5 is covered by a transparent cartridge 15, e.g. a glass plate, allowing the assay site array with the probes inside the micro flow channel 5 to be observed. An analysis with the assay site array is performed by introducing a sample through inlet 2 into the micro flow channel 5 where it passes the array of assay sites and leaves the micro flow channel 5 through outlet 7. An objective 16, optically connected to an optical detector, e.g. a fluorescence microscope, may be focused on the array in the micro flow channel 5 to monitor the chemical reactions at the assay sites.

Figure 14:
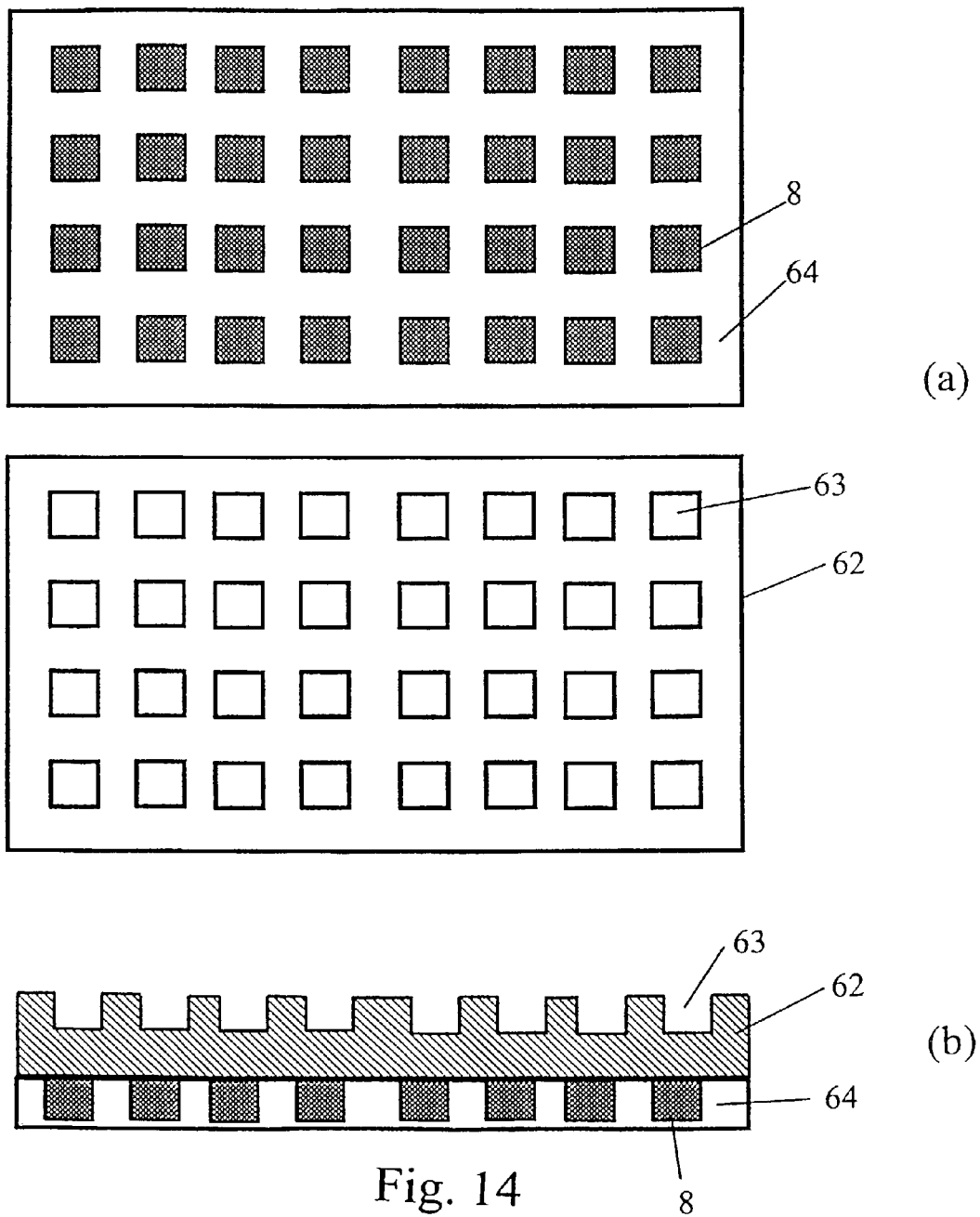
FIG. 14 shows a flow channel having a two-dimensional array of assay sites equipped with magnets to immobilise probes, FIGS. 15(a) and (b) shows two devices each comprising a parallel array of micro flow channels each of which contains an assay site.

FIG. 14 shows another embodiment of the invention comprising a cartridge 62 with a micro flow channel containing assay sites 63 arranged in a two-dimensional array, a cartridge 64 with permanent magnets 8 and a transparent cartridge (not shown) to cover the cartridge 62 with the micro flow channel. The assay sites 63 are formed as small grooves at the surface of the bottom wall of the micro flow channel. The dimensions of the cartridges 62, 64 and the position of the assay sites 63 and the magnets 8 are the same, so if cartridge 62 is placed over cartridge 64 as shown in FIG. 14(*b*), the magnets 8 are located under the assay sites 63.

The embodiments shown in FIG. 12, 13 and 14 may be utilised for hybridisation of DNA as described below. A magnetic carrier including a DNA probe may be immobilised at a specific assay site as described previously. In this way, an array of assay sites is created in a micro flow channel wherein each assay site contains a different DNA probe. Thereafter, a sample containing target molecules is entered into the micro flow channel preferably until the sample has filled the micro flow channel. After the target molecule has been hybridised to a DNA of a specific assay site, a solution of reporter probes, e.g. fluorescence probes, is entered into the flow channel where it binds on the assay site carrying the hybridised DNA. By using a fluorescence detector, e.g. a photomultiplier, focused on the different assay sites the reaction at each assay site can be monitored. By removing the magnetic field on a specific assay site the magnetic material including the DNA probe can be removed, so the process can be reversed. Thus a renewable array of assay sites can be created and wash processes can be implemented in the operation of the array of assay sites.

Figure 15:
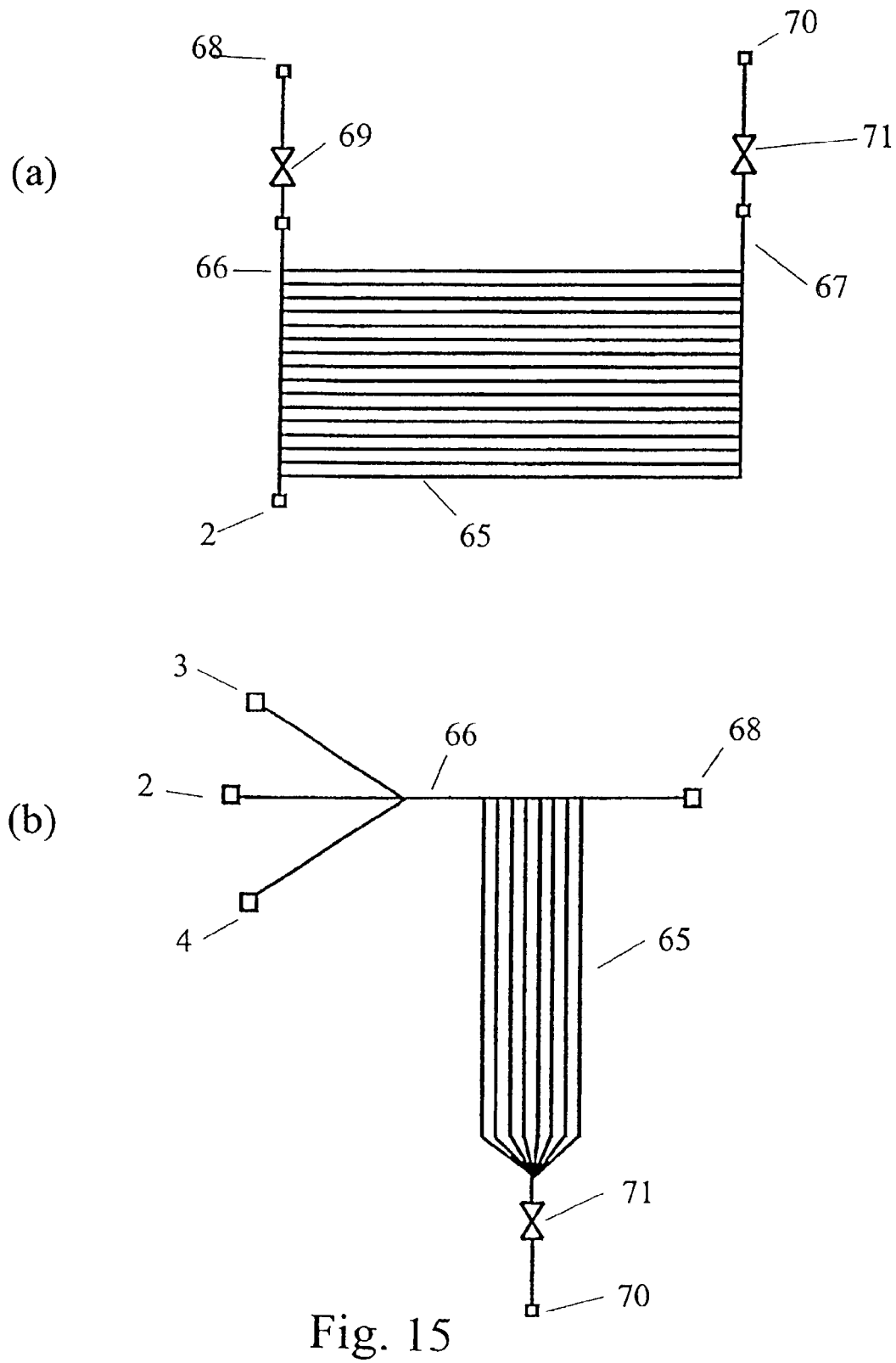

FIG. 15(*a*) shows a device according to the invention for performing a multiple assay analysis in a micro flow system by using a parallel array of assay sites. The system comprises an array of parallel micro flow channels 65 each of which contains one assay site with a specific probe immobilised using e.g. an electrical or magnetic field or by photoactivation as described previously. For example, a cartridge containing a permanent magnet (not shown) can be positioned below the parallel micro flow channels 65 in whereby magnetic probes can be immobilized in the micro flow system using dispensing technology. In this way, a plurality of assay sites may be created in the parallel flow channel 65 array allowing a simultaneous analysis of a sample with a plurality of probes or reagents defined by the number of parallel micro flow channels 65.

The micro flow system consists of two parallel flow channels 66, 67 which are connected via a number of parallel micro flow channels 65 each containing an assay site. An injection flow channel 66 has an inlet 2 and is connected to an outlet 68 via a blocking valve 69, and the waste flow channel 67 is connected to a waste outlet 70 via a blocking valve 71. By blocking one of the two outlets 68, 70 with the blocking valves 69, 71, respectively, it is possible to guide the injected flow through the array of channels 65 containing assay sites or through the injection channel outlet 68, respectively. The flow through all channels 65 containing assay sites is merged into the waste channel 67 and is leaving the system via the waste outlet 70. During passage of the channels 65 containing the assay sites, the sample comes into contact with sensing probes, which are immobilized at the assay sites. Chemical reactions may be detected as described for FIG. 12.

In FIG. 15(b) an alternative embodiment of an array of parallel channels 65 containing assay sites is shown. The micro flow system has three inlet ports 2, 3, 4 to enter different liquids into the micro flow system. By connecting outlet port 68 to a flow restrictor, only one blocking valve 71 is needed to operate the system. If the blocking valve 71 between the channel array 65 and the waste outlet 70 is closed, the channel array 65 is blocked and the flow from inlet 2, 3, 4 will pass the injection channel 66 and leave the micro flow system via outlet 68. When the blocking valve 71 is open, the liquid introduced in the injection channel 66 will flow into the sensor channel array 65 because of the higher flow restriction at outlet 68 compared to waste outlet 70.

Figure 16:
FIG. 16 illustrates the preparation of a micro flow system.
Figure 16:
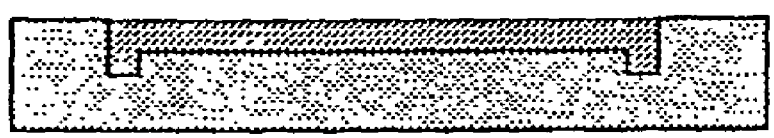
Figure 16:
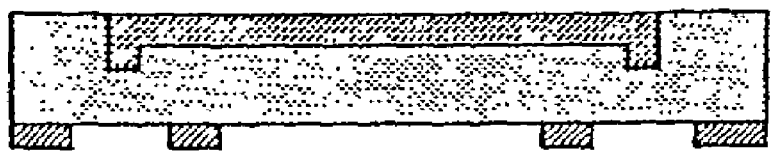
Figure 16:
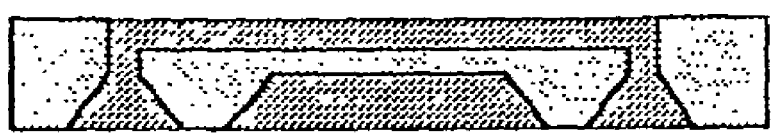
Figure 16:
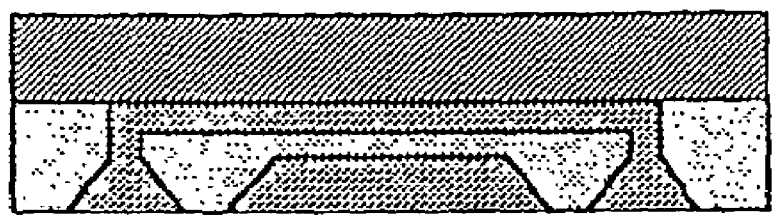

FIG. 16 shows a micro flow system manufactured as a 3-layer sandwich. The central layer is a silicon wafer having a flow channel etched into it. The silicon wafer is covered with a transparent plate, such as a glass plate, having a thickness of, e.g., 0.16 mm. Fluids inside the flow channel may be monitored through the glass plate, e.g. utilising a microscope or other optical detection means. The fluid inlet and outlet are connected to tubings, e.g. fused silica capillary or Teflon tubings, for entering fluids into or discharging fluids from the flow channel. Buffer inlets and the outlet for the sorted particles are not shown. The bottom plate, e.g. made of plastic, facilitates mounting of the tubings.

FIGS. 16(1) to (5) illustrates the following description of the manufacturing and preparation of a micro flow system. A separation flow channel was designed to fit into a system comprising a bonded silicon/glass sandwich. The micro channels were etched into a silicon wafer covered with a boron glass plate having a thickness of 0.2 mm allowing monitoring of the micro channels, using i.e. a microscope. The separation flow channel was fabricated on a 4", 350 μm, <100> silicon wafer. A 1.51 μm layer of $SiO_2$ was applied to the surface of the silicon wafer and was patterned with a mask containing the channel layout. A 2.6 μm layer of photoresist was spun on top of the $SiO_2$ and patterned with a mask defining intermediate holes. The two-step mask consisting of a $SiO_2$ mask and a photoresist mask was used for etching a two level structure with vertical walls by reactive ion etching (RIE) in a $SF_6{:}O_2$ plasma. The holes were initially etched to a depth of 22 μm and then etched deeper together with the channels, which were etched to depths in the range from 40 μm to 100 μm. A layer of 1.8 μm $SiO_2$ was patterned with a mask for inlets and outlets on the back of the silicon wafer. The etching was carried out in KOH at 80° C. and was stopped when all the intermediate holes were clearly visible from the back. Finally, a glass wafer was anodically bonded to the silicon wafer. The micro channels were designed for volumetric flow rates of 0.1 to 200 μl/min with a mean flow speed of maximum 100 (mm/min).

The separation flow channel may be provided with one or two permanent or electromagnets in three different ways:

(a) Rare earth Samarium-Cobalt block magnets of 1.0×1.0×0.5 mm (Goudsmit, Netherlands) may be glued with silicon rubber into the opening slot of the separation flow channel.

(b) Rare earth (Sr) magnetic powder (Tropag, Hamburg, Germany) can be mixed with epoxy 1:1 (v/v) and this magnetic paste may be glued into the opening slot of the separation flow channel yielding a thick film magnetic layer of 1.0×1.0×0.5 mm.

(c) Ferrite steel wool may be glued with silicon rubber into the opening slot of the separation flow channel. A high magnetic field gradient can then be induced inside the opening slots by applying an external magnetic field, e.g. by an electromagnet (Goudsmit, Netherlands) positioned proximate to the separation flow channel.

EXAMPLE 1

A micro flow system with a layout as sketched in FIG. 5(d) with two inlets and two outlets has been tested utilising it for separation of various magnetisable particles. The test conditions are listed below.

| | |
|---|---|
| Particle concentration | $10^7$ particles/ml |
| Total flow rate | 25 μl/min |
| Length flow chip | 3.5 mm |
| Channel width | 250 μm |
| Channel depth | 60 μm |
| Separation time | 2.4 sec |
| Desired particle deflection: | 10 μm |

The separation efficiency (enrichment rate) E and depletion rate 1/E are defined by $$E = \frac{\frac{\%\ \text{positive particles after separation}}{\%\ \text{negative particles after separation}}}{\frac{\%\ \text{positive particles before separation}}{\%\ \text{negative particles before separation}}}$$

For separation of various paramagnetic standard beads of different sizes and paramagnetic field strength, the results are shown in the Table 2.

TABLE 2

| | Separation efficiencies | | | |
|---|---|---|---|---|
| | Size | Separation Efficiency [%][1] | | |
| Paramagnetic Bead | μm | A) | B) | C) |
| Polysciences | | | | |
| 25% iron-oxide | 1–10 | >99 | >99 | 95 |
| 50% iron-oxide | 1–10 | >99 | >99 | 96.5 |
| Paesel + Lorei | | | | |
| Magnetic Affinity | 0.5–1.5 | >99 | >99 | 97.5 |

TABLE 2-continued

Separation efficiencies

| Paramagnetic Bead | Size μm | Separation Efficiency [%][1] | | |
|---|---|---|---|---|
| | | A) | B) | C) |
| Boehringer | | | | |
| Streptavidin Magnetic Dynal | 1 | 90.5 | 88.7 | 89.5 |
| Magnetic Mass Dyal M-450 | 1–10 | 98.0 | >99 | 96.5 |

[1]total flow rates: A) = 10 μl/min, B) = 50 μl/min, C) = 100 μl/min

EXAMPLE 2

Further, the micro flow system used in Example 1 has also been tested by utilising it for separation of Human T-lymphocytes (JURKAT cells). Magnetically stained and unstained JURKAT cells were used to form a heterogeneous cell sample. For magnetic staining of the cells, a CD4-magnetic surface marker from Miltenyi Biotech was used. JURKAT cells were suspended in 1% PBS/BSA to a concentration of $10^7$/ml. Biotin-conjugated CD4 magnetic microbeads were added at 2 μl stock/$10^7$ cells following the manufacturer instruction.

The magnetically stained cells ($10^7$ cells/ml) flowed through the microchip for 10 min. and fluids were collected at the two outlets. Three experiments at different flow rates (5, 25, 50 μl/min) were performed. The same experiments were performed using magnetically unstained cells.

An aliquot of the collected samples was analysed under a microscope and the particles were counted using a Neubauer microscopy chamber. For each experiment 1 μl sample was analysed:

| Run | flow rate [μl/min] | cells [%] at Sort outlet |
|---|---|---|
| Negative (unstained cells) | 5 | <0.1 |
| | 25 | <0.1 |
| | 50 | <0.1 |
| Control[1] | 5 | n.n. |
| | 25 | n.n. |
| | 50 | n.n. |
| Positive (stained cells) | 5 | 95.5 |
| | 25 | 92.8 |
| | 50 | 80.5 |
| Control[1] | 5 | n.n. |
| | 25 | n.n |
| | 50 | n.n. |

[1]using the micro flow system without an integrated magnet

EXAMPLE 3

The system employed for separation of magnetisable particles from a sample is shown in FIG. 4. It comprises two syringe infusion pumps (Harvard Apparatus, Southnatik, Ariz.) that provides constant flow rates of 0.1 to 100 μl/min using a 0.5 ml micro syringe (Hamilton, Bonaduz, Switzerland), a separation flow channel of silicon for the separation of the magnetisable particles, and a collecting unit for collecting of the sorted particles. Two 3-way microvalves (Lee, Parameter AB, Sweden) were integrated into the apparatus for sterile solution handling. All components were interconnected with fused silica capillaries (340 μm id., Supelco, U.S.A.). The SFC was placed under an inverted microscope (Axiovert 100, Zeiss, Germany) for visualisation of the separation procedure. All micro channels and tubing were deactivated by silanisation as described in Blankenstein, G. Scampavia L, Branebjerg J, Larsen U D, Ruzicka J (1996): Flow switch for analyte injection and cell/particle sorting in Analytical Methods and Instrumentation, μTAS '96 conference, 17–22 Nov. 1996, Basel. A FACScan with 488 nm argon laser excitation and collection of forward and side scatter and fluorescence of fluorescein were used (Becton Dickinson, Mountain View, Calif.) for all experiments. Results were collected and analysed using the FACScan research software (Becton Dickinson).

Figure 17:
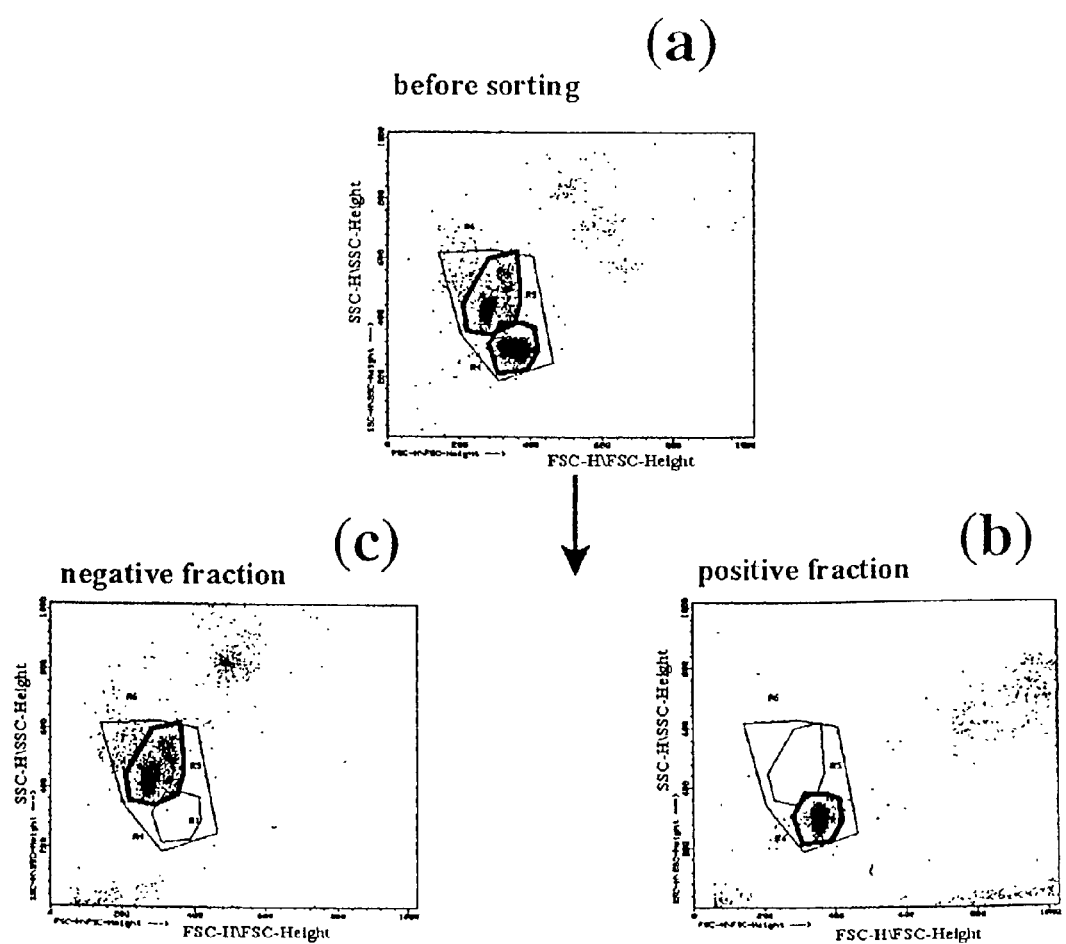
FIG. 17 shows diagrams from the magnetic separation described in Example 3.

Results on the use of a separation flow channel equipped with a permanent magnet optimised for Dynal beads are shown in FIG. 17. A bead suspension of $1.5 \times 10^8$ particles/ml containing a mixture of non labelled magnetic Dynal particles (d: 4.5 μm, M-450) and fluorescence calibration beads (d: 3.2 μm, Dako A/S, Glostrup, Denmark) have been separated. About 1 ml of the non-magnetic, non-deflected fraction was collected at the waste outlet and analysed by flow cytometry (B). To enumerate the positive and negative fractions, two windows were set for the statistic evaluation. Before separation, the sample contained 38.3% fluorescence particles and 55.8% magnetic particles, respectively (a). After sorting by the described system almost all magnetic particles were found in the sorted fraction collected from the sort outlet (b) and non-magnetic particles were found in the negative fraction (c) collected from the waste outlet, respectively. Under optimised conditions, an enrichment rate of 350 was achievable.

EXAMPLE 4

This example concerns enrichment of fetal cells in a sample for magnetic activated cell sorting. A combination of the embodiment of the invention as shown in FIGS. 7 and 10 (upper), optical cytometry, and FIGS. 4 and 10 (lower), magnetic cell separation, provides a powerful apparatus for efficient enrichment of fetal cells in a sample.

Figure 18:
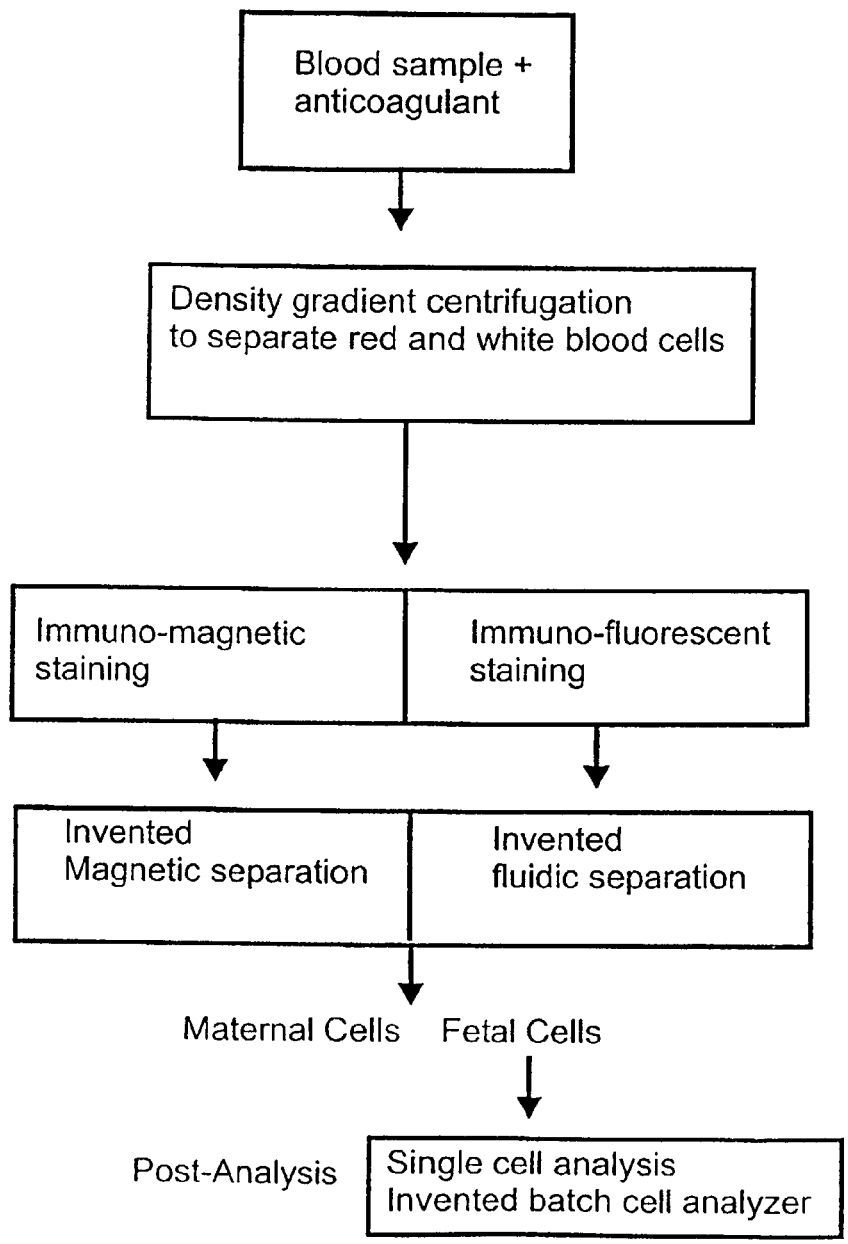
FIG. 18 is a flow chart illustrating a process for separating fetal cells from a maternal blood sample by combining different separation methods as described in Example 4.

The process for increasing the concentration of fetal cell in maternal blood samples involves the following steps (see FIG. 18): (i) A first selection step for removal of the majority of the maternal blood cells based upon their volume, size and density; (ii) A second sorting step for isolation of the fetal blood cells from the remaining maternal blood cells based on immuno-fluorescent separation using a device as described in FIG. 7 and/or based on immuno-magnetic separation using a device as described in FIG. 4. In the examples shown in FIG. 9(b), the magnetic blood sample is first separated in a magnetic separation chamber, followed by a separation due to optical properties of the sample, or two magnetic separations are performed one after the other, see FIG. 9(c), in order to obtain a highly purified product.

An example of sorting of particles of very low concentration from a sample of maternal blood in a non-invasive prenatal screening test is presented in the following paragraph.

Nucleated red blood cells are found in maternal blood in a concentration of 10 to 1000 per ml of all nucleated cells. Bianchi has shown (D. W. Bianchi, Journal of Pediatrics, 1995, 127, 6, p. 847–856) that it is possible to use such cells for genetic screening in prenatal diagnosis. The cell surface marker CD71+ for example, is an appropriate marker to select such cells from maternal blood. Test results demonstrates that magnetic activated cell sorting is powerful enrichment system for sorting and isolating fetal nucleated blood cells from maternal blood. For this the magnetic activated cell micro technology as described in this invention is used. Fetal cells are distinguished and separated from maternal blood by the use of a specific surface marker (CD71) which is only present on the cell membrane of fetal nucleated blood cells. By selectively attaching a magnetic antibody probe to CD71, a magnetic probe is attached substantially exclusively to fetal cells.

EXAMPLE 5

This example concerns depletion of magnetically labelled CD45 positive cells (maternal leukocytes) from a maternal blood sample spiked with cord blood. A flow chip described in FIG. 1 was used in a system as described in FIG. 4. In this experiment a 1:3 spike (fetal/maternal, v/v) was used to demonstrate the performance of the magnetic separation. Heparin was used as an anti-coagulant. The nucleated cells were labelled with CD45 coated magnetic 0.1µ micro particles (Immunicom, U.S.A.), using a monoclonal antibody against CD45 as the first layer. The cell suspension was collected at both outlets 6 and 7 (see FIG. 1). For testing the sorting efficiency, parts of both the collected fractions were analysed on microscope slides. The results showed that most of the cells, more than 95%, collected at the sort outlet 6 were CD45 positive.

EXAMPLE 6

Fluorescence activated cell sorting using the device described in FIG. 7. First results have shown an enrichment factor of more than 300, which indicates that the employed device is a powerful tool for enrichment of rare cellular events.

EXAMPLE 7

An example is given for the embodiment of the invention as described in FIG. 12 for the use of multiple sensor array technology for sensing of a group of analytes in one step. For this purpose, the biosensing components such as antigens or antibodies can be loaded into a specific assay of the flow channel and immobilised there.

Magnetic particles carrying an antigen probe are immobilised on the surface of the micro flow channel by magnetic means. The immobilisation of each probe is exactly specified to a site by switching on a specific electromagnet.

After loading the surface with different groups of antigen probes, the test solution is guided through the flow channel 5 of the microchip. If the sample contains an antibody, which is complementary to one of the different antibodies, it will bind to that specific site where this antibody is immobilised. In a third step, the sample solution has to be removed, and a liquid containing a secondary antibody against the FC region of the first antibody is guided through the micro flow channel. The secondary antibody is coupled to a fluorescence dye allowing the identification of a specific assay site whereto the antibodies has been binded. The device can be used for rapid screening of blood samples, e.g. for identification of bacteria or virus in blood samples having a micro flow channel with virus/bacteria specific antigen probes.

The Invention claimed is:

1. A micro flow system for analysing components of a fluid, the system comprising:
   (a) a member having a flow channel defined therein for guiding a flow of a fluid therethrough;
   (b) first inlet for entering particles into said flow channel;
   (c) first outlet for discharging of fluid from said flow channel;
   (d) a plurality of assay sites located in said flow channel, said assay sites comprising immobilised probes, receptors, reagents, or indicators whereby the fluid may be analysed for a plurality of components while residing in said flow channel; and
   (e) a magnetic field generator positioned proximate to at least some of said the assay sites for generation of a magnetic field proximate to a corresponding assay site whereby at least some of the probes, receptors, reagents, or indicators residing in the flow channel and being susceptible to said field, when generated at a selected assay site, are attracted to and immobilised at said selected assay site.

2. A micro flow system according to claim 1, wherein at least some of the probes, receptors, reagents, or indicators residing in the flow channel and being susceptible to said field, when generated at a selected assay site, are from said selected assay site.

3. A micro flow system according to claim 2, wherein said magnetic field generator comprises permanent magnets positioned on a separate cartridge.

4. A micro flow system according to claim 3, wherein said cartridge is positioned exactly below a second cartridge which has a flow channel with assay sites, inlet, and outlet so that said magnets are accurately positioned below said assay sites in the flow channel.

5. A micro flow system according to claim 1, wherein said member comprises a plurality of flow channels arranged in parallel or in series and each of which has assay sites whereby the fluid containing particles is brought into contact with a large number of assay sites.

6. A micro flow system according to claim 1, wherein said magnetic field generator comprises permanent magnets, electrodes, and electromagnets.

7. A micro flow system according to claim 1, wherein said immobilized probes, receptors, reagents, or indicators comprise antibodies, fluorescence molecules, DNA, RNA, protein dyes, or combinations thereof.

8. A micro flow system according to claim 1, wherein said assay sites are formed as small grooves at the surface of the bottom wall of the micro flow channel.

9. A micro flow system according to claim 1, wherein the plurality of assay sites is arranged as a serial array of assay sites, and wherein the system further comprises a separate cartridge with permanent magnets, said magnets being positioned below said assay sites of the flow channel.

10. A system comprising:
    (a) a substrate defining:
        a flow channel;
        an inlet communicating with the flow channel; and
        an outlet communicating with the flow channel;
    (b) multiple assay sites located in the flow channel, each assay site comprising a probe, receptor, reagent, and/or indicator so immobilized in or on the assay site as to permit interaction with at least a portion of a fluid when the fluid is present in the flow channel; and
    (c) a magnetic field generator so positioned in relation to at least a subset of the assay sites as to permit generation of a magnetic field configured to attract at least some components of the fluid, if present, to only the subset of the assay sites.

* * * * *